United States Patent [19]
Häusler et al.

[11] Patent Number: 5,387,587
[45] Date of Patent: Feb. 7, 1995

[54] CHROMAN DERIVATIVES

[75] Inventors: Günther Häusler; Rolf Gericke, both of Seeheim; Hanns Wurziger, Darmstadt; Manfred Baumgarth, Darmstadt; Inge Lues, Darmstadt; Jacques De Peyer, Seeheim; Rolf Bergmann, Reichelsheim, all of Germany

[73] Assignee: Merck Patent Gesellschaft mit Beschrankter Haftung, Darmstadt, Germany

[21] Appl. No.: 766,725

[22] Filed: Sep. 27, 1991

Related U.S. Application Data

[60] Continuation-in-part of Ser. No. 766,362, Sep. 26, 1991, abandoned, and Ser. No. 655,190, Feb. 13, 1991, abandoned, which is a continuation of Ser. No. 137,201, Dec. 23, 1987, abandoned, and a continuation-in-part of Ser. No. 660,080, Feb. 25, 1991, abandoned, which is a division of Ser. No. 347,710, May 5, 1989, Pat. No. 5,013,853, and a continuation-in-part of Ser. No. 657,941, Feb. 21, 1991, abandoned, which is a continuation of Ser. No. 367,281, Jun. 15, 1989, abandoned, and a continuation-in-part of Ser. No. 420,978, Oct. 13, 1989, abandoned.

[30] Foreign Application Priority Data

| | | | |
|---|---|---|---|
| Dec. 23, 1986 | [DE] | Germany | 3644094 |
| Aug. 7, 1987 | [DE] | Germany | 3726261 |
| May 6, 1988 | [DE] | Germany | 3815504 |
| Jun. 16, 1988 | [DE] | Germany | 3820506 |
| Oct. 14, 1988 | [DE] | Germany | 3835011 |

[51] Int. Cl.$^6$ .................................. C07D 405/12
[52] U.S. Cl. .................................. 514/254; 514/253; 514/256; 514/269; 514/337; 514/274; 544/238; 544/405; 544/408; 544/309; 544/298; 544/310; 544/315; 544/319; 544/230; 546/269; 546/15
[58] Field of Search ................ 514/254, 253; 544/408, 544/336, 405

[56] References Cited

U.S. PATENT DOCUMENTS

| | | | |
|---|---|---|---|
| 4,510,152 | 4/1985 | Faruk | 546/196 |
| 4,631,282 | 12/1986 | Cassidy | 514/254 |
| 4,687,779 | 8/1987 | Evans | 546/196 |
| 4,738,963 | 4/1988 | Hamilton et al. | 514/254 |
| 4,999,371 | 3/1991 | Englert | 514/337 |
| 5,013,853 | 5/1991 | Gericke et al. | 544/408 |
| 5,028,711 | 7/1991 | Stenzel | 546/196 |
| 5,043,344 | 8/1991 | Englert et al. | 514/337 |
| 5,071,871 | 12/1991 | Blarer et al. | 514/337 |
| 5,112,839 | 5/1992 | Gericke et al. | 514/337 |
| 5,112,972 | 5/1992 | Gericke et al. | 514/253 |
| 5,116,849 | 5/1992 | Garcia et al. | 514/337 |
| 5,118,694 | 6/1992 | Attwood | 514/254 |
| 5,130,322 | 7/1992 | Gericke et al. | 514/337 |
| 5,143,924 | 9/1992 | Gericke et al. | 514/253 |
| 5,154,726 | 10/1992 | Jackson | 8/142 |
| 5,238,937 | 8/1993 | Gericke et al. | 544/336 |
| 5,284,838 | 2/1994 | Garcia et al. | 514/89 |

FOREIGN PATENT DOCUMENTS

| | | | |
|---|---|---|---|
| 0273262 | 7/1988 | European Pat. Off. | 546/269 |
| 0296975 | 12/1988 | European Pat. Off. | |
| 0312432 | 4/1989 | European Pat. Off. | 546/269 |
| 3815504 | 11/1989 | Germany | |

OTHER PUBLICATIONS

Bergmann et al. I Jour Med Chem vol. 33 pp. 492–502 (1990).
Bergmann et al. II Jour Med Chem vol. 33 pp. 2759–2767 (1990).

*Primary Examiner*—Donald G. Daus
*Attorney, Agent, or Firm*—Millen, White, Zelano, & Branigan

[57] ABSTRACT

Chroman derivatives of the formula I

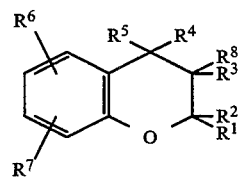

wherein $R^1$ to $R^8$ have the meanings defined herein, and their salts have an effect on the cardiovascular system.

18 Claims, No Drawings

CHROMAN DERIVATIVES

CROSS-REFERENCE TO RELATED DISCLOSURES

This application is also a continuation in part of U.S. Ser. No. 766,362, filed Sep. 26, 1991, also the entirety of which is incorporated by reference which is a continuation-in-part of U.S. Ser. No. 07/655,190, filed on Feb. 13, 1991, abandoned, which is a continuation of U.S. Ser. No. 07/137,201, filed on Dec. 23, 1987 abandoned; 07/660,080, filed on Feb. 25, 1991 abandoned, which is a divisional of U.S. Ser. No. 07/347,710 of May 5, 1989, now U.S. Pat. No. 5,013,853; 07/657,941, filed on Feb. 21, 1991, abandoned, which is a continuation of U.S. Ser. No. 07/367,281 of Jun. 15, 1989 abandoned; Ser. No. 07/420,978 of Oct. 13, 1989 abandoned, whose entire disclosures are hereby incorporated by reference herein. This application is related to the following disclosures: Bergmann et al., J. Med. Chem. 33 (1990) 492–504; Bergmann et al., J. Med. Chem 33 (1990) 2760–2767; U.S. Pat. No. 4,952,696; and FRG P 38 35 011.4 of Oct. 14, 1988, the entireties of all of which are hereby incorporated by reference.

BACKGROUND OF THE INVENTION

It is an object of the invention to provide new compounds having valuable properties, particularly compounds which can be used for the preparation of medicaments.

Upon further study of the specification and appended claims, further objects and advantages of this invention will become apparent to those skilled in the art.

These objects are achieved by providing chroman derivatives of the formula I:

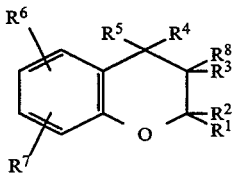

wherein
$R^1$ is A,
$R^2$ and $R^8$ are each H or A,
$R^1$ and $R^2$ together are also alkylene having 3–6 C atoms,
$R^3$ is H, OH, OA or OAc,
$R^4$ is H,
$R^3$ and $R^4$ together are also a bond,
$R^5$ is a pyridyl-Z-, pyridazinyl-Z-, pyrimidinyl-Z-, pyrazinyl-Z-, oxo-dihydro-pyridyl-Z-, oxo-dihydropyridazinyl-Z-, oxo-dihydro-pyrimidinyl-Z-, oxo-dihydro-pyrazinyl-Z-, 1H-2-pyridon-1-yl, 1H-6-pyridazinon-1-yl, 1H-2-pyrimidinon-1yl, 1H-6-pyrimidinon-1-yl, 1H-2-pyrazinon-1-yl or 1H-2-thiopyridon-1-yl radical which is unsubstituted or monosubstituted or disubstituted by A, F, Cl, Br, I, OH, AO, OAc, SH, $NO_2$, $NH_2$, AcNH, HOOC and/or AOOC, it being also possible for these radicals to be partially hydrogenated,
$R^6$ and $R^7$ are each H, A, HO, AO, CHO, ACO, ACS, HOOC, AOOC, AO—CS, ACOO, A—CS—O, hydroxyalkyl having 1–6 C atoms, mercaptoalkyl having 1–6 C atoms, $NO_2$, $NH_2$, NHA, $NA_2$, CN, F, Cl, Br, I, $CF_3$, ASO, $ASO_2$, AO—SO, AO—$SO_2$, AcNH, AO—CO—NH, $H_2$NSO, NANSO, $A_2$NSO, $H_2NSO_2$, HANSO$_2$, $A_2NSO_2$, $H_2$NCO, HANCO, $A_2$NCO, $H_2$NCS, HANCS, $A_2$NCS, ASONH, $ASO_2$NH, AO-SONH, AOSO$_2$NH, ACO-alkyl, nitroalkyl, cyanoalkyl, A—C(=NOH) or A—E(=$NNH_2$),
Z is O, S or NH,
A is alkyl having 1–6 C atoms,
alkyl is alkylene having 1–6 C atoms and
Ac is alkanoyl having 1–8 C atoms or aroyl having 7–11 C atoms, and also to salts thereof.

In the foregoing, selection of variables defined together is made independently.

It has been found that the compounds of formula I and their physiologically acceptable salts possess valuable pharmacological properties and are well tolerated. Thus they exhibit an action on the cardiovascular system in which, as a rule, a selective attack on the coronary system can be observed at fairly low doses and a hypotensive effect can be observed at fairly high doses. Examples of effects on the coronary system are a decrease in resistance and increase in flow, while the effect on the heart rate remains small. The compounds also have a relaxing action on various smooth muscle organs (the gastro-intestinal tract, the-respiratory system and the uterus). The action of the compounds can be measured by means of methods which are known per se, such as are indicated, for example, EP-A1-76,075, EP-A1-173,848 or AU-A 45,547/85 (Derwent Farmdoc No. 86,081,769) and by K. S. Meesmann et al., Arzneimittelforschung 25 (11), 1975, 1770–1776. Examples of suitable experimental animals are mice, rats, guinea-pigs, dogs, cats, monkeys or pigs.

The compounds can therefore be used as active compounds for medicaments in human and veterinary medicine. They can also be used as intermediate products for the preparation of further active compounds for medicaments.

In the formulae indicated, A is an alkyl group which is preferably unbranched and has 1–6, preferably 1–4 and especially 1, 2 or 3, C atoms, specifically preferably methyl, and also preferably ethyl, propyl, isopropyl, butyl or isobutyl, and also preferably sec.-butyl, tert.-butyl, pentyl, isopentyl (3-methylbutyl), hexyl or isohexyl (4-methylpentyl).

If $R^1$ and $R^2$ together are alkylene, the alkylene group is preferably unbranched and is specifically preferably —$(CH_2)_n$— wherein n is 3, 4, 5 or 6.

The group "alkyl" is preferably —$CH_2$— or —$CH_2CH_2$—.

Ac is preferably alkanoyl having 1–6, in particular 1, 2, 3 or 4, C atoms, specifically preferably formyl or acetyl, and also preferably propionyl, butyryl, isobutyryl, pentanoyl or hexanoyl, and also preferably benzoyl, o-, m- or p-toluyl, 1-naphthoyl or 2-naphthoyl.

$R^1$ and $R^2$ are preferably each alkyl, particularly each methyl or ethyl and preferably each methyl.

$R^3$ and $R^4$ are preferably, together, a bond. If $R^4$ is H, $R^3$ is preferably OH, O—CHO or O—COCH$_3$.

$R^5$ is preferably unsubstituted 1H-2-pyridon-1-yl or 1H-2-pyrazinon-1-yl and also preferably unsubstituted 1H-6-pyridazinon-1-yl, 4,5-dihydro-1H-6-pyridazinon-1-yl, 1H-2-pyrimidinon-1-yl, 1H-6-pyrimidinon-1-yl or 1H-2-thiopyridon-1-yl. If $R^5$ is a substituted pyridone or thiopyridone ring, this ring is preferably monosubstituted in the 3-, 4- or 5-position or is disubstituted in the 3-position and the 5-position. Substituents which are particularly preferred are $NO_2$ and $NH_2$, and also AOOC, OA, Cl, Br and NHCOCH$_3$. Substituted radicals R$^5$ which are particularly preferred are specifically 3-, 4-, 5- or 6-methoxy-, 3-, 4-, 5- or 6-acetoxy-, 3-, 5- or 6-chloro-, 3-nitro- or 5-nitro-, 3-amino- or 5-amino-, 3-carboxy- or 5-carboxy-, 3-methoxycarbonyl- or 5-methoxycarbonyl-, 3-ethoxycarbonyl- or 5-ethoxycarbonyl-, 3-acetamido- or 5-acetamido-, 3,5-dichloro-, 3,5-dibromo-, 3-chloro-5-nitro-, 3-nitro-5-chloro-, 3-bromo-5-nitro-, 3-nitro-5-bromo-, 3,5-dinitro-, 3-chloro-5-amino-, 3-amino-5-chloro-, bromo-5-amino-, 3-amino-5-bromo-, 3-chloro-5-acetamido-, 3-acetamido-5-chloro-, 3-bromo-5-acetamido- and 3-acetamido-5-bromo-1H-2-pyridon-1-yl or -1H-2-thiopyridon-1-yl,1H-3-, 1H-4- or 1H-5-ethoxycarbonyl-6-pyridazinon-1-yl.

R$^5$ can also preferably be: 3,4-dihydro-1H-2-pyridon-1-yl, 2,3-dihydro-6H-2-pyridon-1-yl, 5,6-dihydro-1H-2-pyridon-1-yl, 2,3-dihydro-1H-6-pyridazinon-1-yl, 1,2-dihydro-5H-6-pyridazinon-1-yl, 3,4-dihydro-1H-2-pyrimidinon-1-yl, 1,6-dihydro-3H-2-pyrimidinon-1-yl, 5,6-dihydro-1H-2-pyrimidinon-1-yl, 2,3-dihydro-1H-6-pyrimidinon-1-yl, 1,2-dihydro-5H-6-pyrimidinon-1-yl, 4,5-dihydro-1H-6-pyrimidinon-1-yl, 3,4-dihydro-1H-2-pyrazinon-1-yl, 1,6-dihydro-3H-2-pyrazinon-1-yl, 5,6-dihydro-1N-2-pyrazinon-1-yl, 3,4-dihydro-1H-2-thiopyridon-1-yl, 2,3-dihydro-6H-2-thiopyridon-1-yl or 5,6-dihydro-1H-2-thiopyridon-1-yl.

Furthermore, R is preferably 6-hydroxy-3-pyridazinyl-Z(=1,6-dihydro-6-oxo-3-pyridazinyl-Z-) or 2-hydroxy-4-pyridyl-Z- (=1,2-dihydro-2-oxo-4-pyridyl-Z-), and in addition preferably unsubstituted 2-, 3- or 4-pyridyl-Z-, 2-, 4- or 5-pyrimidinyl-Z-, 3-, 4- or 5-pyridazinyl-Z or pyrazinyl-Z-, hydroxypyridyl-Z- such as 3-, 4-, 5- or 6-hydroxy-2-pyridyl-Z-, 2-, 4- or 5-hydroxy-3-pyridyl-Z-, 3-hydroxy-5-pyridyl-Z-, 2-hydroxy-5-pyridyl-Z-; hydroxypyridazinyl-Z- such as 4- or 5-hydroxy-3-pyridazinyl-Z-, 3-, 5- or 6-hydroxy-4-pyridazinyl-Z-; hydroxypyrimidinyl-Z- such as 4- or 5-hydroxy-2-pyrimidinyl-Z-, 2-, 5- or 6-hydroxy-4-pyrimidinyl-Z-, 2- or 4-hydroxy-5-pyrimidinyl-Z-; hydroxypyrazinyl-Z- such as 3-, 5- or 6-hydroxy-2-pyrazinyl-Z-; dihydroalkyloxopyridyl-Z-, such as 1,2-dihydro-l-methyl-2-oxo-3-, -4-, -5- or -6-pyridyl-Z-, 1,2-dihydro-1-ethyl-2-oxo-3-, -4-, -5- or -6-pyridyl-Z-; dihydroalkyloxopyridazinyl-Z- such as 1,6-dihydro-1-methyl-6-oxo-3-, -4or -5-pyridazinyl-Z-, 1,6-dihydro-1-ethyl-6-oxo-3-, -4-, or -5-pyridazinyl-Z-; alkoxypyridyl-Z- such as 3-, 4-, 5- or 6-methoxy-2-pyridyl-Z-, 2-, 4- or 5-methoxy-3-pyridyl-Z-, 2- or 3-methoxy-4-pyridyl-Z-, 2-methoxy-5-pyridyl-Z-, 2- or 3-ethoxy-4-pyridyl-Z-; alkoxy-pyridazinyl -Z- such as 4-, 5- or 6-methoxy-3-pyridazinyl-Z-, 4-, 5- or 6-ethoxypyridazinyl-Z-, 3-, 5- or 6-methoxy-4-pyridazinyl-Z-, 3-, 5- or 6-ethoxy-4-pyridazinyl-Z-; alkoxypyrimidinyl-Z- such as 4- or 5-methoxy-2-pyrimidinyl-Z-, 2-, 5- or 6-methoxy-4-pyrimidinyl-Z-, 2- or 4-methoxy-5-pyrimidinyl-Z-: alkoxypyrazinyl-Z- such as 3-, 5- or 6-methoxy-2-pyrazinyl-Z-; aminopyridyl-Z- such as 3-, 4-, 5- or 6-amino-2-p-pyridyl-Z-, 2-, 4- or 5-amino-3-pyridyl-Z-, 2- or 3-amino-4-pyridyl-Z-, 2-amino-5-pyridyl-Z-; aminopyridazinyl-Z- such as 4-, 5- or 6-amino-3-pyridazinyl-Z-, 3-, 5- or 6-amino-4-pyridazinyl-Z-; aminopyrimidinyl-Z- such as 4- or 5-amino-2-pyrimidinyl-Z-; 2-, 5- or 6-amino-4-pyrimidinyl-Z-, 2- or 4-amino-5-pyrimidinyl-Z-; aminopyrazinyl-Z- such as 3-, 5- or 6-amino-2-pyrazinyl-Z-; mercaptopyridyl-Z- such as 3-, 4-, 5- or 6-mercapto-2-pyridyl-Z-, 2-, 4- or 5-mercapto-3-pyridyl-Z-, 2-(=1,2-dihydro-2-thioxo-4-pyridyl-Z-) or 3-mercapto-4-pyridyl-Z-, 2-mercapto-5-pyridyl-Z-; mercaptopyridazinyl-Z- such as 4-, 5- or 6-mercapto-3-pyridazinyl-Z- (=1,6-dihydro-6-thioxo-3-pyridazinyl-Z-), 3-, 5- or 6-mercapto-4-pyridazinyl-Z-; mercaptopyrimidinyl-Z- such as 4- or 5-mercapto-2-pyrimidinyl-Z-, 2-, 5- or 6-mercapto-4-pyrimidinyl-Z-, 2- or 4-mercapto-5-pyrimidinyl-Z-; mercaptopyrazinyl-Z- such as 3-, 5- or 6-mercapto-2-pyrazinyl-Z-.

Radicals of the type R$^3$ which contain a hydroxyl or mercapto group adjacent to a ring N atom may also exist in the tautomeric lactam or thiolactam form, as indicated above in individual cases.

The radical -Z- is preferably —O—.

In R$^6$ and R$^7$ the symbols are preferably as follows:

A: methyl and also ethyl;
AO: methoxy and also ethoxy;
ACO: acetyl and also propionyl;
ACS: thioacetyl and also thiopropionyl;
AOOC: methoxycarbonyl and also ethoxycarbonyl;
AO-CS: methoxythiocarbonyl and also ethoxythiocarbonyl;
ACOO: acetoxy and also propionoxy;
A-CS-O: thio(no)acetoxy and also thio(no)propionoxy;
hydroxyalkyl: hydroxymethyl, 1-hydroxyethyl or 2-hydroxyethyl;
mercaptoalkyl: mercaptomethyl, 1-mercaptoethyl or 2-mercaptoethyl;
NHA: methylamino and also ethylamino;
NA$_2$: dimethylamino and also diethylamino;
ASO: methylsulfinyl and also ethylsulfinyl;
ASO$_2$: methylsulfonyl and also ethylsulfonyl;
AO-SO: methoxysulfinyl and also ethoxysulfinyl;
AO-SO$_2$: methoxysulfonyl and also ethoxysulfonyl;
Ac-NN: acetamido and also formamido, propionamido benzamido;
AO-CO-NH: methoxycarbonylamino and also ethoxycarbonylamino;
HANSO: methylaminosulfinyl and also ethylaminosulfinyl;
A$_2$NSO: dimethylaminosulfinyl and also diethylaminosulfinyl;
HANSO$_2$:methyl aminosulfonyl and also ethylaminosulfonyl;
A$_2$NSO$_2$: dimethylaminosulfonyl and also diethylaminosulfonyl;
HANCO: N-methyl carbamoyl and also N-ethylcarbamoyl;
A$_2$NOC: N,N-dimethylcarbamoyl and also N,N-diethylcarbamoyl;
HANCS: N-methyl thiocarbamoyl and also N-ethylthiocarbamoyl;
A$_2$NCS: N,N-dimethylthiocarbamoyl and also N,N-diethylthiocarbamoyl;
ASONH: methylsulfinylamino and also methylsulfinylamino;
ASO$_2$NH: methylsulfonylamino and also ethylsulfonylamino;
AOSONH: methoxysulfinylamino and also ethoxysulfinylamino;
AOSO$_2$NH: methoxysulfonylamino and also ethoxysulfonylamino;
ACO-alkyl: 2-oxopropyl, 2-oxobutyl, 3-oxobutyl or 3-oxopentyl;
nitroalkyl: nitromethyl, 1-nitroethyl or 2-nitroethyl;
cyanoalkyl: cyanomethyl, 1-cyanoethyl or 2-cyanoethyl;

A-C(=NOH): 1-oximinoethyl and also 1-oximino-propyl;

A-C(=NNH$_2$): 1-hydrazonoethyl and also 1-hydrazonopropyl.

The radicals R$^6$ and R$^7$ are preferably in the 6-position and 7-position of the chroman system. They can, however, also be in the 5- and 6-, 5- and 7-, 5- and 8-, 6- and 8-position and in the 7- and 8-position.

One of the radicals R$^6$ and R$^7$ is preferably H, while the other is different from H. This other radical is preferably in the 6-position, but can also be in the 5-, 7- or 8-position, and is preferably CN or NO$_2$, and also preferably CHO, ACO (particularly acetyl), AOOC (particularly methoxycarbonyl or ethoxycarbonyl) or ACOO (particularly acetoxy), and also preferably F, Cl, Br, I, CF$_3$, H$_2$NCO, H$_2$NCS or NH$_2$.

The radical R$^8$ is preferably H and furthermore preferably methyl or ethyl. Accordingly, the invention relates particularly to those compounds of the formula I in which at least one of the radicals mentioned has one of the preferred meanings mentioned above. Some preferred groups of compounds can be expressed by means of the formulae Ia to Ii below, which correspond to the formula I and in which the radicals not indicated in detail have the meaning indicated in the formula I, but in which in Ia: R$^1$ and R$^2$ are each A;
in Ib: R$^1$ and R$^2$ are each CH$^3$;
in Ic: R$^1$ and R$^2$ together are alkylene having 3–6 C atoms;
in Id: R$^5$ is 1H-2-pyridon-1-yl, 1H-2-pyrazinon-1-yl, 1H-6-pyridazinon-1-yl, 4,5-dihydro-1H-6-pyridazinon-1-yl, 1H-2-pyrimidinon-1-yl, 1H-6-pyrimidinon-1-yl, 1H-2-thiopyridon-1-yl, 3-, 4-, 5- or 6-methoxy-, 3-, 4-, 5- or 6-acetoxy-, 3-, 5- or 6-chloro-, 3-nitro- or 5-nitro-, 3-amino- or 5-amino-, 3-carboxy- or 5-carboxy-, 3-methoxycarbonyl- or 5-methoxycarbonyl-, 3-ethoxycarbonyl- or 5-ethoxycarbonyl-, 3-acetamido- or 5-acetamido-, 3,5-dichloro-, 3,5-dibromo-, 3-chloro-5-nitro-, 3-nitro-5-chloro-, 3-bromo-5-nitro-, 3-nitro-5-bromo-, 3,5 -dinitro-, 3-chloro-5-amino-, 3-amino-5-chloro-, 3-bromo-5-amino-, 3-amino-5-bromo-, 3-chloro-5-acetamido-, 3-acetamido-5-chloro-, 3-bromo-5-acetamido- or 3-acetamido-5-bromo-1H-2-pyridon-1-yl or -1H-2-thiopyridon-1-yl, 1H-3-, 1H-4- or 1H-5-ethoxycarbonyl-6-pyridazinon-1-yl in Ie: R$^5$ is 1H-2-pyridon-1-yl or 1H-2-pyrazinon-1yl
in If: R$^5$ is 1H-2-pyridon-1-yl;
in Ig: R$^1$ and R$^2$ are each CH$_3$ and R$^5$ is 1H-2-pyridon-1-yl, 1H-2-pyrazinon-1-yl, 1H-6-pyridazinon-1-yl, 4,5-dihydro-1H-6-pyridazinon-1-yl, 1H-2-pyrimidinon-1-yl, 1H-6-pyrimidinon-1-yl , 1H-2-thiopyridon-1-yl, 3-, 4-, 5- or 6-methoxy-, 3-, 4-, 5- or 6-acetoxy-, 3-, 5- or 6-chloro-, 3-nitro- or 5-nitro-, 3-amino- or 5-amino-, 3-carboxy- or 5-carboxy, 3-methoxycarbonyl- or 5-methoxycarbonyl-, 3-ethoxycarbonyl- or 5-ethoxycarbonyl-, 3-acetamido- or 5-acetamido-, 3,5-dichloro-, 3,5-dibromo-, 3-chloro-5-nitro-, 3-nitro-5-chloro-, 3-bromo-5-nitro-, 3-nitro-5-bromo-, 3,5-dinitro-, 3-chloro-5-amino-, 3-amino-5-chloro-, 3-bromo-5-amino-, 3-amino-5-bromo-, 3-chloro-5-acetamido-, 3-acetamido-5-chloro-, 3-bromo-5-acetamido- or 3-acetamido-5-bromo-1H-2-pyridon-1-yl or -1H-2-thiopyridon-1H-6-pyridazinon-1-yl, 4,5-dihydro-1H-6 1-yl, 1H-3-, 1H-4- or 1H-5-ethoxycarbonyl-6-pyridazinon-1-yl in Ih: R$^1$ and R$^2$ are each CH$_3$ and R$^5$ is 1H-2-pyridon-1-yl or 1H-2-pyrazinon-1-yl; and in Ii: R$^1$ and R$^2$ are each CH$_3$ and R$^5$ is 1H-2-pyridon-1-yl.

Compounds of the formulae I' and Ia' to Ii' which correspond to the formulae I and Ia to Ii, but in which in each case R$^3$ additionally is OH, OCHO or OCOCH$_3$ and R$^4$ is additionally H are also preferred.

Compounds of the formulae I" and Ia" to Ii" which correspond to the formulae I and Ia to Ii, but in which in each case R$^3$ and R$^4$ together are additionally a bond are also preferred.

Compounds of the formulae I, I', I", Ia to Ii, Ia' to Ii' and Ia" to Ii" in which, in each case, additionally (a) R$^6$ is other than H and R$^7$ is H;
(b) R$^6$ other than H and is in the 6-position and R$^7$ is H;
(c) R$^6$ is NO$_2$, CN, CHO, ACO, HOOC, AOOC, ACOO, F, Cl, Br, I, CF$_3$, H$_2$NCO, H$_2$NCS or NH$_2$ and R$^7$ is H;
(d) R$^6$ is NO$_2$, CN, CHO, ACO, HOOC, AOOC, ACOO, F, Cl, Br, I, CF$_3$, H$_2$NCO, H$_2$NCS or NH$_2$ and is in the 6-position and R$^7$ is H;
(e) R$^6$ is NO$_2$, CN, CHO, CH$_3$CO, CH$_3$OOC, , C$_2$H$_5$OOC or CH$_3$COO and R$^7$
(f) R$^6$ is NO$_2$, CN, CHO, CH$_3$CO, CH$_3$OOC, C$_2$H$_5$OOC or CH$_3$COO and is in the 6-position and R$^7$ is H;
(g) R$^6$ is NO$_2$ or CN and R$^7$ is H;
(h) R$^6$is NO$_2$ or CN and is in the 6-position and R$^7$ is H;
(i) R$^6$ is CN and R$^7$ is H;
(j) R$^6$ is CN and is in the 6-position and R$^7$is H, are also preferred.

Among the compounds of all preceding formulae, those are preferred wherein (a) R$^8$ is H, (b) R$^8$ is CH$_3$.

Incidentally, in the preceding and following text, the radicals R$^1$ to R$^8$, A, "alkyl" and Ac have the meanings indicated in formula I unless anything to the contrary is expressly indicated.

The invention also relates to a process for the preparation of the compounds of the formula I and their salts, which is characterized in that a 3,4-epoxychroman of the formula II

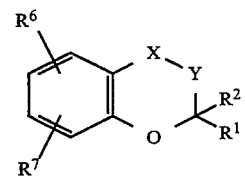

II wherein —X—Y— is

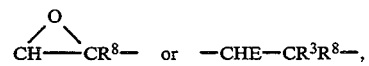

or —CHE—CR$^3$R$^8$—, E is Cl, Br, I or a reactively esterified OH group, and R$^1$, R$^2$, R$^3$, R$^6$, R$^7$ and R$^8$ have the meaning indicated in formula I, is reacted with a compound of the formula III

R$^5$—H    III wherein R$^5$ has the meaning indicated in formula I, or with one of its reactive derivatives,
and/or a compound of the formula I, wherein R$^3$ is OH and R$^4$ is H is dehydrated, and/or in a compound of the formula I one or more of the radicals $R^3$, $R^5$, $R^6$ and/or $R^7$ are converted into to other radicals $R^3$, $R^5$, $R^6$ and/or $R^7$ and/or a basic compound of the formula I is converted into one of its acid addition salts by treatment with an acid.

The compounds of the formula I are, incidentally, prepared by methods which are known per se, such as are described in the literature (for example in the standard works, such as Houben-Weyl, Methoden der organischen Chemie ("Methods of Organic Chemistry"), Georg-Thieme-Verlag, Stuttgart; Organic Reactions, John Wiley & Sons, Inc., New York; and in the patent applications indicated above) and specifically under reaction conditions which are known and suitable for the reactions mentioned. In this regard it is also possible to make use of variants which are known per se but are not mentioned here in detail.

If desired, the starting materials can also be formed in situ in such a way that they are not isolated from the reaction mixture, but are immediately reacted further to give the compounds of the formula I.

The compounds of the formula I are preferably prepared by reacting compounds of the formula II with compounds of the formula III, preferably in the presence of an inert solvent, at temperatures between about 0° and 150°.

Starting materials of the formula II with

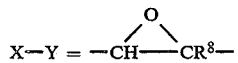

(3,4-epoxychromans) are preferred.

The starting materials II and III are usually known. If they are not known, they can be prepared by methods which are known per se. Thus, the starting materials of the formula II

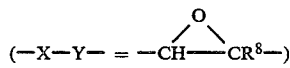

are obtainable by reacting 2-hydroxyacetophenones of the formula 2-HO-$R^6R^7C_6H_2$-COCH$_3$ with ketones of the formula $R^1$-CO-$R^2$ to give corresponding 4-chromanones of the formula IVa

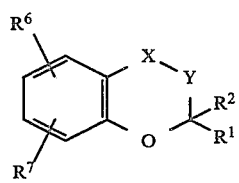

IVa —X—Y— = —CO—CH$_2$—
IVb —X—Y— = —CO—C(=CH—$R^9$)—
IVc —X—Y— = —CHOH—CHR$^8$—
IVd —X—Y— = —CH=CR$^8$—
IVe —X—Y— = —CHBr—CR$^8$OH— if desired condensing with aldehydes of the formula $R^9$-CHO ($R^9$=alkyl having 1-5 C atoms) to give 3-alkylidene-4-chromanones of the formula IVb, reducing, for example with NaBH$_4$, to give chromanols of the formula IVc, dehydrating, for example with p-toluenesulfonic acid, to give chromenes of the formula IVd and oxidizing, for example with 3-chloroperbenzoic acid. The last-mentioned oxidation can also be carried out in a number of steps. Thus, for example, the bromohydrins of the formula IVe can initially be prepared using N-bromosuccinimide in aqueous solution and HBr can subsequently be eliminated from these using a base, for example sodium hydroxide solution.

The chromenes of the formula IVd can also be obtained by condensation of salicylaldehydes of the formula 2-HO-$R^6R^7C_6H_2$-CHO with ketones of the formula $R^1$-CO-CH$_2$-$R^8$ to give hydroxyketones of the formula 2-HO-$R^6R^7C_6H_2$-CH|CR$^8$-CO-$R^1$, reaction with organolithium compounds of the formula $R^2$-Li and subsequent hydrolysis to give diols of the formula 2-HO-$R^6R^7C_6H_2$-CH=CR$^8$-CR$^1R^2$-OH, and cyclization with elimination of water.

In compounds of the formula II (—X—Y—=—CHE—CR$^3R^8$-), possible "reactively esterified OH groups" are in particular esters with alkylsulfonic acids (in which the alkyl group contains 1-6 C atoms) or with arylsulfonic acids (in which the aryl group contains 6-10 C atoms). These compounds are obtainable from the 4-chromanols of the formula IVc by reacting with an inorganic acid halide such as PCl$_3$, PBr$_3$, SOCl$_2$ or SOBr$_2$ or with a sulfonyl chloride such as methanesulfonyl or p-toluenesulfonyl chloride.

Starting materials of the formula II ($R^8$ H) can be obtained by reacting propargyl chlorides of the formula HC≡C—CR$^1R^2$—Cl with phenols of the formula $R^6R^7C_6H_3$OH to give phenol ethers of the formula $^6R^7C_6H_3$O—CR$^1R^2$—C≡CH, cyclizing the products to give chromenes corresponding to formula IVd ($R^8$=H), adding on a molecule of HOBr to give the bromohydrin of formula IVe ($R^8$ =H) and dehydrobrominating the product (for method cf., for example, EP-A1-76,075).

Suitable reactive derivatives of III are the corresponding salts, for example the Na or K salts, which can also be formed in situ.

It is preferable to carry out the reaction of II with III in the presence of a base. Examples of suitable bases are alkali metal hydroxides, hydrides or amides or alkaline earth metal hydroxides, hydrides or amides, such as NaOH, KOH, Ca(OH)$_2$, NaH, KH, CaH$_2$, NaNH$_2$ or KNH$_2$, and also organic bases, such as triethylamine or pyridine, which can also be used in excess and can then at the same time act as the solvent.

Suitable inert solvents are, in particular, alcohols,-.such as methanol, ethanol, isopropanol, n-butanol or tert.-butanol; ethers, such as diethyl ether, diisopropyl ether, tetrahydrofuran or dioxane; glycol ethers, such as ethylene glycol monomethyl or monoethyl ether (methylglycol or ethylglycol) or ethylene glycol dimethyl ether (diglyme); ketones, such as acetone or butanone; nitriles, such as acetonitrile; nitro compounds, such as nitromethane or nitrobenzene;. esters, such as ethyl acetate; amides, such as dimethylformamide (DMF), dimethylacetamide or phosphoric acid hexamethyltriamide; sulfoxides, such as dimethyl sulfoxide (DMSO); chlorinated hydrocarbons, such as methylene dichloride, chloroform, trichloroethylene, 1,2-dichloroethane or carbon tetrachloride; or hydrocarbons, such as benzene, toluene or xylene. Mixtures of these solvents with one another are also suitable.

The epoxide II can also be prepared in situ, for example by the action of a base on the corresponding bromohydrin IVe.

Different products of formula I can be formed by the reaction of II with III, dependent in particular from the structure of the starting materials and from the reaction conditions.

For instance, the formation of compounds of formula I containing an oxygen bridge ($R^5$=unsubstituted or substituted pyridyl-oxy, pyridazinyl-oxy, pyrimidinyl-oxy, pyrazinyl-oxy, oxo-dihydro-pyridyl-oxy, oxo-dihydropyridazinyl-oxy, oxo-dihydro-pyrimidinyl-oxy or oxodihydro-pyrazinyl-oxy) is favored if the compound III contains at least one OH group as a substituent in addition to the lactame or lactime group and/or if the reaction is carried out under relatively mild conditions, e.g., in the presence of a weak base such as pyridine in an alcohol. For instance, from 2,2,3-trimethyl-3,4-epoxy-6-cyano-chromane ("IIb") and 1H-2-pyridone with NaH in DMSO there are formed predominantly 2,2,3 -trimethyl-4-(1H-2-pyridon-1-yl )-6-cyano-2H-chromene ("C") and 2,2,3-trimethyl-4-(1H-2-pyridon-1-yl )-6-cyano-chroman-3-ol ("D") whereas with pyridine in ethanol there are formed about equal parts of "D" and 2,2,3-trimethyl-4-(2-pyridyl-oxy)-6-cyano-chroman-3-ol. From 2,4-dihydroxypyridine (=4-hydroxy-1H-2-pyridone) and IIb in pyridine/ethanol there are formed 2,2,3 -trimethyl-4-(2-hydroxy-4-pyridyl-oxy )-6-cyano-chroman-3-ol and 2,2,3 -trimethyl -4-(4-hydroxy-1H-2 -pyridon-1-yl )-6-cyano-chroman-3-ol in a weight ratio of about 9:1.

In each single case optimal reaction conditions can be worked out easily. The reaction products, can be separated and isolated without difficulties, e.g., by crystallization and/or chromatography.

A compound of the formula I wherein $R^3$ is ON and $R^4$ is H can be converted by treatment with a dehydrating agent into a compound of the formula I wherein $R^3$ and $R^4$ together are a bond. This is effected, for example, by the action of one of the bases indicated, for example Nail, in one of the solvents indicated, for example DRSO, at temperatures between 0° and 150°.

It is also possible to convert one or more of the radicals $R^3$, $R^5$, $R^6$ and/or $R^7$ in a compound of the formula I into other radicals $R^3$, $R^5$, $R^6$ and/or $R^7$.

For example, it is possible to replace an H atom by a halogen atom by halogenation or to replace an H atom by a nitro group by nitration and/or to reduce a nitro group to an amino group and/or to alkylate or acylate an amino or hydroxyl group and/or to convert a cyano group into a carboxyl group (for example by means of HCl in water/methanol at 20°–100° ) or into a formyl group (for example by means of Raney nickel in water-/acetic acid/pyridine in the presence of sodium phosphate) or into a carbamoyl group (for example by means of KOH in tert.-butanol) or into a thiocarbamoyl group (for example by means of $H_2S$ in pyridine/triethylamine) and/or to convert a -CO-NH-group (for example by means of $P_2S_5$ or by means of Lawesson reagent in toluene) into a -CS-NH- or -C(SH)=N- group.

A nitration reaction is carried out under customary conditions, for example using a mixture of concentrated $HNO_3$ and concentrated $H_2SO_4$ at temperatures between 0° and 30°. If at least one of the substituents $R^6$ and $R^7$ is an electronegative group, such as CN or $NO_2$, the nitration takes place predominantly on the $R^5$ radical; otherwise mixtures in which the nitro groups can be on the $R^5$ radical or in the chroman ring are usually obtained.

Analogous considerations apply to halogenation, which can be carried out, for example, using elementary chlorine or bromine in one of the customary inert solvents at temperatures between about 0° and 30°.

A primary or secondary amino group and/or an OH group can be converted by treatment with alkylating agents into the corresponding secondary or tertiary amino group and/or alkoxy group. Examples of suitable alkylating agents are compounds of the formulae A-Cl, A-Br or A-I or corresponding sulfuric acid esters or sulfonic acid esters, such as methyl chloride, bromide or iodide, dimethyl sulfate or methyl p-toluenesulfonate, It is also possible, for example, to introduce one or two methyl groups by means of formaldehyde in the presence of formic acid, The alkylation is preferably carried out in the presence or absence of one of the inert solvents mentioned, for example DMF, at temperatures between about 0° and about 120°, and a catalyst can also be present, preferably a base, such as potassium tert.-butylate or NaH.

Suitable acylating agents for the acylation of amino or hydroxyl groups are preferably the halides (for example chlorides or bromides) or anhydrides of carboxylic acids of the formula Ac-OH, for example acetic anhydride, propionyl chloride, isobutyryl bromide, formic/acetic anhydride or benzoyl chloride. It is possible to add a base, such as pyridine or triethylamine, during the acylation. It is preferable to carry out the acylation in the presence or absence of an inert solvent, for example a hydrocarbon, such as toluene, a nitrile, such as acetonitrile, an amide, such as DMF, or an excess of a tertiary base, such as pyridine or triethylamine, at temperatures between about 0° and about 160° preferably between 20° and 120°. Formylation can also be carried out by means of formic acid in the presence of pyridine.

A base of the formula I can be converted into the appropriate acid addition salt by means of an acid. Acids which afford physiologically acceptable salts are particularly suitable for this reaction. Thus it is possible to use inorganic acids, for example sulfuric acid, nitric acid, hydrogen halide acids, such as hydrochloric acid or hydrobromic acid, phosphoric acids, such as orthophosphoric acid, and sulfamic acid, and also organic acids, in particular aliphatic, alicyclic, araliphatic, aromatic or heterocyclic, monobasic or polybasic carboxylic, sulfonic or sulfuric acids, for example formic acid, acetic acid, propionic acid, pivalic acid, diethylacetic acid, malonic acid, succinic acid, pimetic acid, fumaric acid, maleic acid, lactic acid, tartaric acid, malic acid, benzoic acid, salicylic acid, 2-phenylpropionic or 3-phenylpropionic, acid, citric acid, gluconic acid, ascorbic acid, nicotinic acid, isonicotinic acid, methanesulfonic or ethanesulfonic acid, ethanedisulfonic acid, 2-hydroxyethanesulfonic acid, benzenesulfonic acid, p-toluenesulfonic acid, naphthalene monosulfonic and naphthalene disulfonic acids, and laurylsulfuric acid, Salts with physiologically unacceptable acids, for example picrates, can be used to purify the compounds of the formula I.

The compounds of the formula I can contain one or more chiral centers. When they are prepared, therefore, they can be obtained in the form of racemates or, if optically active starting materials are used, also in an optically active form. If the compounds have two or more chiral centers, they can be produced, in the synthesis, as mixtures of racemates, from which the individual racemates can be isolated in a pure form, for example by recrystallization from inert solvents. Thus, for example, compounds of the formula I wherein $R^1$ is $R^2$, $R^3$ is OH and $R^4$ is H have two chiral centers; however, when they are prepared by reacting II with III the product formed is very predominantly only one racemate having the substituents $R^3$=OH and $R^5$ in the trans-position. The resulting racemates can, if desired, be separated into their enantiomers by mechanical or chemical means, in accordance with methods known per se. Thus diastereomers can be formed from the racemate by reacting it with an optically active separating agent. Examples of suitable separating agents for basic compounds of the formula I are optically active acids, such as the D-forms and l-forms of tartaric acid, dibenzoyltartaric acid, diacetyltartaric acid, camphorsulfonic acids, mandelic acid, .malic acid or lactic acid. Carbinols (I, $R^3$=ON) can also be esterified by means of chiral acylating reagents, for example D-α-methylbenzyl isocyanate or l-α-methylbenzyl isocyanate, and can then be separated (cf. EP-A1-120,428). The different forms of the diastereomers can be separated in a manner known per se, for example by fractional crystallization, and the enantiomers of the formula I can be liberated from the diastereomers in a manner known per se. It is also possible to carry out separation of enantiomers by chromatography over optically active supporting materials.

Optically active compounds of formula I can, of course, be obtained from optically active starting materials, f.e. from the enantiomeric forms of the epoxides of formula II.

The compounds of the formula I and their physiologically acceptable salts can be used for the preparation of pharmaceutical formulations, particularly by a non-chemical route. In this regard they can be brought into a suitable dosage form together with at least one solid, liquid and/or semi-liquid excipient or auxiliary and, if appropriate, in combination with one or more further active compounds.

The invention also relates to agents, in particular pharmaceutical formulations, containing at least one compound of the formula I and/or one of its physiologically acceptable salts.

These formulations can be-used as medicaments in human or veterinary medicine. Suitable excipients are organic or inorganic substances which are suitable for enteral (for example oral) or parenteral administration or topical application and which do not react with the new compounds, for example water, vegetable oils, benzyl alcohols, polyethylene glycols, glycerol triacetate, gelatine, carbohydrates, such as lactose or starch. magnesium stearate, talc, lanolin or petroleum jelly. Tablets, coated tablets, capsules, syrups, elixirs or drops are especially used for oral administration, suppositories are used for rectal administration, solutions, preferably oily or aqueous solutions, and also suspensions, emulsions or implants are used for parenteral administration, while ointments, creams pastes, lotions, gels, sprays, foams, aerosols, solutions (for example solutions in alcohols such as ethanol or isopropanol, acetonitrile, DMF, dimethylacetamide, 1,2-propanediol or their mixtures with each other and/or with water) or powders are used for topical application. The new compounds can also be lyophilized,and the resulting lyophilizates can be used, for example, for the preparation of injection preparations. Liposomal preparations are in particular also suitable for topical application. The formulations described can be sterilized and/or can contain auxiliaries, such as lubricants, preservatives, stabilizers and/or wetting agents, emulsifiers, salts for influencing the osmotic pressure, buffer substances, colorants and flavorings and/or aroma substances. They can, if desired, also contain one or more further active compounds, for example one or more further active compounds, for example one or more vitamins.

The compounds of the formula I and their physiologically acceptable salts can be administered to humans or animals, in particular mammals, such as monkeys, dogs, cats, rats or mice, and can be used in the therapeutic treatment of the human or animal body and in combating diseases, particularly in the therapy and/or prophytaxis of disorders of the cardiovascular system, in particular decompensated cardiac insufficiency, angina pectoris, arrhythmia, peripheral or cerebral vascular diseases and also states of diseases which are associated with high blood pressure. They are also usable for combating disorders which are connected with changes in the non-vascular musculature, for example urinary incontinence. In addition, they are useful as bronchodilators, and thus for treatment of bronchial asthma, typically in the same dosage ranges as discussed below.

In this regard, the substances according to the invention are generally administered analogously to known anti-anginal agents or hypotensive agents, for example nicorandil or BRl-34915 [2,2-dimethyl-4-(2-oxo-1-pyrrolidinyl)-6-cyanochroman-3-ol; cf. EP-A1-173,848], preferably in dosages between about 0.01 and 5 mg, especially between 0.02 and 0.5 mg, per dosage unit. The daily dosage is preferably between about 0.0001 and 0.1, in particular between 0.0003 and 0.01 mg/kg of body weight.

A preferred daily dosage range for the treatment of angina pectoris is 0.003 to 0.03 mg/kg of body weight.

The particular dose for each specific patient depends, however, on a very wide variety of factors, for example on the effectiveness of the particular compound employed, on the age, body weight, general state health, sex, on the diet, on the time and method of administration, on the rate of excretion, the combination of medicaments and the severity of the particular disease against which the therapy is used. Oral administration is preferred.

Preferred agents of this invention are "A" of Example 1 below and "(−)-B" of Example 25 below, e.g., for treating angina pectoris and/or for use as a coronary vasodilator.

The compounds of the formula I and their salts are also suitable, particularly in the case of topical use, for the treatment of alopecia, including androgenic alopecia and Alopecia areata. The pharmaceutical formulations used especially for this purpose are those which are suitable for topical treatment of the scalp and which are mentioned above. They contain about 0.005 to 10, preferably 0.5 to 3, % by weight of at least one compound of the formula I and/or at least one of its salts. In other respects these compounds can be used against alopecia analogously to the instructions in WO 88/00822.

The term "partially hydrogenated" in the definition of $R^5$ above means that, in the radicals in question, instead of one C=C or one C=N double bond there may be a saturated CH—CH or CH—NH bond; with other words, this term means to include the dihydro derivatives of the cited radicals.

Without further elaboration, it is believed that one skilled in the art can, using the preceding description; utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire text of all applications, patents and publications, if any, cited above and below are hereby incorporated by reference.

The entire disclosures of FRG P 37 26 261.0, filed Aug. 7, 1987, and P 36 44 094.9, filed Dec. 23, 1986, are incorporated by reference herein.

The entire disclosures of FP, G P 38 20 506, filed Jun. 16, 1988; and FRG P 38 15 504, filed May 6, 1988, are incorporated by reference herein.

EXAMPLES

In the following examples, "customary working up" means as follows:

If necessary, water is added, the mixture is extracted with an organic solvent, such as ethyl acetate, the phases are separated, the organic phase is dried over sodium sulfate, filtered and evaporated and the product is purified by chromatography and/or crystallization. $\beta = a_D^{20}$ in methanol, c=1.

Example 1

A mixture of 20.1 g of 2,2-dimethyl-3,4-epoxy-6-cyano-chroman ("IIa"), 9.5 g of 1H-2-pyridone ("pyridone"), 3 g of an 80% dispersion of NaH in paraffin oil and 600 ml of DMSO is stirred for 16 hours at 20°, poured into water and extracted with ethyl acetate. The extract is evaporated and the residue is chromatographed over silica gel. 2,2-Dimethyl-4-(1H-2-pyridon-1-yl)-6-cyano-2H-chromene ("A"; m.p. 146°–148°) is eluted with methylene dichloride, and then 2,2-dimethyl-4-(1H-2-pyridon-1-yl)-6-cyanochroman-3-ol ("B"; m.p. 244°) is eluted with ethyl acetate; the ratio of "A" to "B" is about 9:7.

The following are obtained analogously:

2,2-dimethyl-4-(1H-2-thiopyridon-1-yl)-6-cyano-2H-chromene 2,2-dimethyl-4-(1H-2-thiopyridon-1-yl)-6-cyanochroman-3-ol 2,2-dimethyl-4-(1H-3-chloro-2-pyridon-1-yl)-6-cyano-2H-chromene 2,2-dimethyl-4-(1H-3-chloro-2-pyridon-1-yl)-6-cyanochroman-3-ol 2,2-dimethyl-4-(1H-5-chloro-2-pyridon-1-yl)-6-cyano-2H-chromene, m.p. 185°–188°

2,2-dimethyl-4-(1H-5-chloro-2-pyridon-1-yl)-6-cyanochroman-3-ol, m.p. 268°–270°

2,2-dimethyl-4-(1H-6-chloro-2-pyridon-1-yl)-6-cyano-2H-chromene 2,2-dimethyl-4-(1H-6-chloro-2-pyridon-1-yl)-6-cyanochroman-3-ol 2,2-dimethyl-4-(2-hydroxy-3-pyridyl-oxy)-6-cyanochroman-3-ol, m.p. 262°–265°

2,2-dimethyl-4-(1H-4-hydroxy-2-pyridon-1-yl)-6-cyano-2H-chromene, m.p. 290°–295°

2,2-dimethyl-4-(2-hydroxy-4-pyridyl-oxy)-6-cyanochroman-3-ol, m.p. 248°–250°

2,2-dimethyl-4-(2-hydroxy-5-pyridyl-oxy)-6-cyanochroman-3-ol; m.p. 256.5°–258°

2,2-dimethyl-4-(1H-3-methoxy-2-pyridon-1-yl)-6-cyano-2H-chromene 2,2-dimethyl-4-(1H-3-methoxy-2-pyridon-1-yl)-6-cyanochroman-3-ol, m.p. 245°–248°

2,2-dimethyl-4-(1H-3-acetoxy-2-pyridon-1-yl)-6-cyano-2H-chromene 2,2-dimethyl-4- (1H-3-acetoxy-2-pyridon-1-yl)-6-cyanochroman-3-ol, m.p. 260°–263°

2,2-dimethyl-4-(1H-3-nitro-2-pyridon-1-yl)-6-cyano-2H-chromene, m.p. 148°–150°

2,2-dimethyl-4-(1H-3-nitro-2-pyridon-1-yl)-6-cyanochroman-3-ol, m.p. 240°–242°

2,2-dimethyl-4-(1H-5-nitro-2-pyridon-1-yl)-6-cyano-2H-chromene, m.p. 214°–216°

2,2-dimethyl-4-(1H-5-nitro-2-pyridon-1-yl)-6-cyanochroman-3-ol, m.p. 249°–251°

2,2-dimethyl-4-(1H-3-amino-2-pyridon-1-yl)-6-cyano-2H-chromene 2,2-dimethyl-4-(1H-3-amino-2-pyridon-1-yl)-6-cyanochroman-3-ol, m.p. 213°–215°

2,2-dimethyl-4-(1H-5-amino-2-pyridon-1-yl)-6-cyano-2H-chromene, m.p. 180°

2,2-dimethyl-4-(1H-5-amino-2-pyridon-1-yl)-6-cyanochroman-3-ol, m.p. 260°–264°

2,2-dimethyl-4-(1H-3-acetamido-2-pyridon-1-yl)-6-cyano-2H-chromene 2,2-dimethyl -4-(1H-3-acetamido-2-pyridon-1-yl)-6-cyanochroman-3-ol, m.p. 274°–276°

2,2-dimethyl -4-(1H-5-acetamido-2-pyridon-1-yl)-6-cyano-2H-chromene, 255°–256°

2,2-dimethyl -4-(1H-5-acetamido-2-pyridon-1-yl)-6-cyanochroman-3-ol, m.p. 303°–305°

2,2-dimethyl -4-(1H-3-carboxy-2-pyridon-1-yl)-6-cyano-2H-chromene 2,2-dimethyl-4-(1H-3-carboxy-2-pyridon-1-yl)-6-cyanochroman-3-ol, m.p. 250°–253°

2,2-dimethyl-4-(1H-5-carboxy-2-pyridon-1-yl)-6-cyano-2H-chromene 2,2-dimethyl-4-(1H-5-carboxy-2-pyridon-1-yl)-6-cyanochroman-3-ol, m.p. 238°–240°

2,2-dimethyl-4-(1H-3,5-dichloro-2-pyridon-1-yl)-6-cyano-2H-chromene, m.p. 230°–232°

2,2-dimethyl-4-(1H-3,5-dichloro-2-pyridon-1-yl)-6-cyanochroman-3-ol, m.p. 167°–170°

2,2-dimethyl-4-(1H-3,5-dibromo-2-pyridon-1-yl)-6-cyano-2H-chromene, m.p. 268°–270°

2,2-dimethyl-4-(1H-3,5-dibromo-2-pyridon-1-yl)-6-cyanochroman-3-ol, m.p. 207°–209°

2,2-dimethyl-4-(1H-3-chloro-5-nitro-2-pyridon-1-yl)-6-cyano-2H-chromene 2,2-dimethyl-4-(1H-3-chloro-5-nitro-2-Pyridon-1-yl)-6-cyanochroman-3-ol 2,2-dimethyl-4-(1H-3-nitro-5-chloro-2-pyridon-1-yl)-6-cyano-2H-chromene 2,2-dimethyl-4-(1H-3-nitro-5-chloro-2-pyridon-1-yl)-6-cyanochroman-3-ol 2,2-dimethyl-4-(1H-3-bromo-5-nitro-2-pyridon-1-yl)-6-cyano-2H-chromene 2,2-dimethyl-4-(1H-3-bromo-5-nitro-2-pyridon.-1-yl)-6-cyanochroman-3-ol 2,2-dimethyl-4-(1H-3-nitro-5-bromo-2-pyridon-1-yl)-6-cyano-2H-chromene 2,2-dimethyl-4-(1H-3-nitro-5-bromo-2-pyridon-1-yl)-6-cyanochroman-3-ol 2,2-dimethyl-4-(1H-3,5-dinitro-2-pyridon-1-yl)-6-cyano-2H-chromene 2,2-dimethyl-4-(1H-3,5-dinitro-2-pyridon-1-yl)-6-cyanochroman-3-ol 2,2-dimethyl-4-(1H-3-chloro-5-amino-2-pyridon-1-yl)-6-cyano-2H-chromene 2,2-dimethyl-4-(1H-3-chloro-5-amino-2-pyiridon-1-yl)-6-cyanochroman-3-ol 2,2-dimethyl-4-(1H-3-amino-5-chloro-2-pyridon-1-yl)-6-cyano-2H-chromene
2,2-dimethyl-4-(1H-3-amino-5-chloro-2-pyridon-1-yl)-6-cyanochroman-3-ol
2,2-dimethyl-4-(1H-3-bromo-5-amino-2-pyridon-1-yl)-6-cyano-2H-chromene
2,2-dimethyl-4-(1H-3-bromo-5-amino-2-pyridon-1-yl)-6-cyanochroman-3-ol
2,2-dimethyl-4-(1H-3-amino-5-bromo-2-pyridon-1-yl)-6-cyano-2H-chromene
2,2-dimethyl-4-(1H-3-amino-5-bromo-2-pyridon-1-yl)-6-cyanochroman-3-ol
2,2-dimethyl-4-(1H-3-chloro-5-acetamido-2-pyridon-1-yl)-6cyano-2H-chromene
2,2-dimethyl-4-(1H-3-chloro-5-acetamido-2-pyridon-1-yl)-6-cyanochroman-3-ol
2,2-dimethyl-4-(1H-3-acetamido-5-chloro-2-pyridon-1-yl)-6-cyano-2H-chromene
2,2-dimethyl-4-(1H-3-acetamido-5-chloro-2-pyridon-1-yl)-6-cyanochroman-3-ol
2,2-dimethyl-4-(1H-3-bromo-5-acetamido-2-pyridon-1-yl)-6-cyano-2 H-chromene
2,2-dimethyl-4-(1H-3-bromo-5-acetamido-2-pyridon-1-yl)-6-cyanochroman-3-ol
2,2-dimethyl-4-(1M-3-acetamido-5-bromo-2-pyridon-1-yl)-6-cyano-2 H-chromene
2,2-dimethyl-4-(1H-]-acetamido-5-bromo-2-pyridon-1-yl)-6-cyanochroman-3-ol
2,2-dimethyl-4-(1H-2-pyridon-1-yl)-6-nitro-2H-chromene, m.p. 158°
2,2-dimethyl-4-(1H-2-pyridon-1-yl)-6-nitrochroman-3-ol, m.p. 229°–231°
2,2-dimethyl-4-(1H-2-thiopyridon-1-yl)-6-nitro-2H-chromene
2,2-dimethyl-4-(1H-2-thiopyridon-1-yl)-6-nitrochroman-3-ol
2,2-dimethyl-4-(1H-3-chloro-2-Pyridon-1-yl)-6-nitro-2H-chromene
2,2-dimethyl-4-(1H-3-chloro-2-pyridon-1.-yl)-6-nitrochroman-3-ol
2,2-dimethyl-4-(1H-2-chloro-2-pyridon-1-yl)-6-nitro-2H-chromene
2,2-dimethyl-4-(1H-5-chloro-2-pyridon-1-yl)-6-nitrochroman-3-ol
2,2-dimethyl-4-(1H-6-chloro-2-pyridon-1-yl)-6-nitro-2H-chromene
2,2-dimethyl-4-(1H-6-chloro-2-pyridon-1-yl)-6-nitrochroman-3-ol
2,2-dimethyl-4-(1N-3-methoxy-2-pyridon-1-yl)-6-nitro-2H-chromene
2,2-dimethyl-4-(1H-3-methoxy-2-pyridon-1-yl)-6-nitrochroman-3-ol
2,2-dimethyl-4-(1H-3-acetoxy-2-pyridon-1-yl)-6-nitro-2H-chromene
2,2-dimethyl-4-(1H-]-acetoxy-2-pyridon-1-yl)-6-nitrochroman-5-ol
2,2-dimethyl-4-(1H-3-nitro-2-pyridon-1-yl)-6-nitro-2H-chromene
2,2-dimethyl-4-(1H-3-nitro-2-pyridon-1-yl)-6-nitrochroman-3-ol
2,2-dimethyl-4-(1H-5-nitro-2-pyridon-1-yl)-6-nitro-2H-chromene
2,2-dimethyl-4-(1H-5-nitro-2-pyridon-1-yl)-6-nitrochroman-3-ol
2,2-dimethyl-4-(1H-3-amino-2-pyridon-1-yl)-6-nitro-2H-chromene
2,2-dimethyl-4-(1H-3-amino-2-pyridon-1-yl)-6-nitrochroman-3-ol
2,2-dimethyl-4-(1H-5-amino-2-pyridon-1-yl)-6-nitro-2H-chromene
2,2-dimethyl-4-(1H-5-amino-2-pyridon-1-yl)-6-nitrochroman-3-ol
2,2-dimethyl-4-(1H-3-acetamido-2-pyridon-1-yl)-6-nitro-2H-chromene
2,2-dimethyl-4-(1H-3-acitamido-2-pyridon-1-yl)-6-nitrochroman-3-ol
2,2-dimethyl-4-(1H-5-acetamido-2-pyridon-1-yl)-6-nitro-2H-chromene
2,2-dimethyl-4-(1H-5-acetamido-2-pyridon-1-yl)-6-nitro-chroman-3-ol
2,2-dimethyl-4-(1H-3-carboxy-2-pyridon-1-yl)-6-nitro-2H-chromene
2,2-dimethyl-4-(1H-3-carboxy-2-pyridon-1-yl)-6-nitrochroman-3-ol
2,2-dimethyl-4-(1H-5-carboxy-2-pyridon-1-yl)-6-nitro-2H-chromene
2,2-dimethyl-4-(1H-5-carboxy-2-pyridon-1-yl)-6-nitrochroman-3-ol
2,2-dimethyl-4-(1H-3,5-dichloro-2-pyridon-1-yl)-6-nitro-2H-chromene
2,2-dimethyl-4-(1H-3,5-dichloro-2-pyridon-1-yl)-6-nitrochroman-3-ol
2,2-dimethyl-4-(1H-3,5-dibromo-2-pyridon-.1-yl)-6-nitro-2H-chromene
2,2-dimethyl-4-(1H-3,5-dibromo-2-pyridon-1-yl)-6-nitrochroman-3-ol
2,2-dimethyl-4-(1H-3-chloro-5-nitro-2-pyridon-1-yl)-6-nitro-2H-chromene
2,2-dimethyl-4-(1H-3-chloro-5-nitro-2-pyridon-1-yl)-6-nitrochroman-3-ol
2,2-dimethyl-4-(1H-3-nitro-5-chloro-2-pyridon-1-yl)-6-nitro-2H-chromene
2,2-dimethyl-4-(1H-3-nitro-5-chloro-2-pyridon-1-yl)-6-nitrochroman-3-ol
2,2-dimethyl-4-(1H-3-bromo-5-nitro-2-pyridon-1-yl)-6-nitro-2H-chromene
2,2-dimethyl-4-(1H-3-bromo-5-nitro-2-pyridon-1-yl)-6-nitrochroman-3-ol
2,2-dimethyl-4-(1H-3-nitro-5-bromo-2-pyridon-1-yl)-6-nitro- 2H-chromene
2,2-dimethyl -4-(1H-3-nitro-5-bromo-2-pyridon-1-yl)-6-nitrochroman-3-ol
2,2-dimethyl-4-(1H-3,5-dinitro-2-pyridon-1-yl )-6-nitro-2H-chromene
2,2-dimethyl-4-(1H-3,5-dinitro-2-pyridon-1-yl )-6-nitrochroman-3-ol
2,2-dimethyl-4-(1H-3-chloro-5-amino-2-pyridon-1-yl )-6-nitro-2H-chromene
2,2-dimethyl-4-(1H-3-chloro-5-amino-2-pyridon-1-yl )-6-nitrochroman-3-ol
2,2-dimethyl-4-(1H-3-amino-5-chloro-2-pyridon-1-yl )-6-nitro-2H-chromene
2,2-dimethyl-4-(1H-3-amino-5-chloro-2-pyridon-1-yl )-6-nitrochroman-3-ol
2,2-dimethyl-4-(1H-3-bromo-5-amino-2-pyridon-1-yl )-6-nitro-2H-chromene
2,2-dimethyl-4-(1H-3-bromo-5-amino-2-pyr idon-1-yl )-6-nitrochroman-3-ol
2,2-dimethyl-4-(1H-3-amino-5-bromo-2-pyr don- 1 -yl) -6-nitro-2H-chromene
2,2-dimethyl-4-(1H-3-amino-5-bromo-2-pyr t don-1-yl ) -6-nitrochroman-3-ol
2,2-dimethyl-4-(1H-3-chloro-5-acetamido-2-pyridon-1-yl )-6-nitro-2H-chromene
2,2-dimethyl-4-(1H-3-chloro-5-acetamido-2-pyridon-1-yl )-6-nitrochroman-3-ol 2,2-dimethyl-4-(1H-3-acetamido-5-chloro-2-pyridon-1-yl)-6-nitro-2H-chromene
2,2-dimethyl-4-(1H-3-acetamido-5-chloro-2-Pyridon-1-yl)-6-nitrochroman-3-ol
2,2-dimethyl-4-(1H-3-bromo-5-acetamido:2-pyridon-1-yl)-6-nitro-2H-chromene
2,2-dimethyl-4-(1H-3-bromo-5-acetamido-2-pyridon-1-yl)-6-nitrochroman-3-ol
2,2-dimethyl-4-(1H-3-acetamido-5-bromo-2-pyridon-1-yl)-6-nitro-2H-chromene
2,2-dimethyl-4-(1H-3-acetamido-5-bromo-2-pyridon-1-yl)-6-nitrochroman- 3-ol
2,2-dimethyl-4-(1H-2-pyridon-1-yl)-6-acetyl-2H-chromene, m.p. 148°–150°
2,2-dimethyl-4-(1H-2-pyridon-1-yl)-6-acetylchroman-3-ol, m.p. 257°–259°
2,2-dimethyl-4-(1H-2-pyridon-1-yl)-6-methoxycarbonyl-2H-chromene, m.p. 126°–127°
2,2-dimethyl-4-(1H-2-pyridon-1-yl)-6-methoxycarbonylchroman-3-ol, m.p. 267°–267.5°
2,2-dimethyl-4-(1H-2-pyridon-1-yl )-6-ethoxycarbonyl-2H-chromene
2,2-dimethyl-4-(1H-2-pyridon-1-yl)-6-ethoxycarbonylchroman-3-ol, m.p. 213°
2,2-dimethyl-4-(1H-2-pyridon-1-yl)-6-fluoro-2H-chromene
2,2-dimethyl-4-(1H-2-pyridon-1-yl)-6-fluorochroman-3-ol
2,2-dimethyl-4-(1H-2-pyridon-1-yl)-6-chloro-2H-chromene
2,2-dimethyl-4-(1H-2-pyridon-1-yl)-6-chlorochroman-3-ol
2,2-dimethyl-4-(1H-2-pyridon-1-yl)-6-trifluoromethyl-2H-chromene
2,2-dimethyl-4-(1H-2-pyridon-1-yl)-6-trifluoromethylchroman-3-ol
2,2-dimethyl-4-(1H-2-pyridon-1-yl)-6-acetamido-2H-chromene
2,2-dimethyl-4-(1H-2-pyridon-1-yl)-6-acetamidochroman-3-ol
2,2-dimethyl-4-(1H-2-pyridon-1-yl)-6-carbamoyl-2H-chromene, m.p.250°–252°
2,2-dimethyl-4-(1H-2-pyridon-1-yl)-6-carbamoylchroman-3-ol
2,2-dimethyl-4-(1H-2-pyridon-1-yl)-6-thiocarbamoyl-2H-chromene
2,2-dimethyl-4-(1H-2-pyridon-1-yl)-6-thiocarbamoytchroman-3ol
2,2-dimethyl-4-(1H-2-pyridon-1-yl)-7-cyano-2H-chromene
2,2-dimethyl-4-(1H-2-pyridon-1-yl)-7-cyanochroman-3-ol
2,2-dimethyl-4-(1H-2-pyridon-1-yl)-6-acetamido-7-nitro-2H-chromene
2,2-dimethyl-4-(1H-2-pyridon-1-yl)-6-acetamido-7-nitrochroman-3-ol
2,2-dimethyl-4-(1H-3-nitro-2-pyridon-1-yl)-6-methoxycarbonyl-2H -chromene
2,2-dimethyl-4-(1H-3-nitro-2-pyridon-1-yl)-6-methoxycarbonylchroman-3-ol
2,2-tetramethylene-4-(1H-2-pyridon-1-yl)-6-cyano-2H-chromene, m.p. 181°–183°
2,2-tetramethylene-4-(1H-2-pyridon-1-yl)-6-cyano-3-chromanol, m.p. 227°–230°
2,2-pentamethylene-4-(1H-2-pyridon-1-yl)-6-cyano-2H-chromene, m.p. 202°–204°
2,2-pentamethylene-4-(1H-2-pyridon-1-yl)-6-cyano-3-chromanol, m.p. 240°–242°
2,2-dimethyl-4-(1H-2-pyridazinon-1-yl)-6-cyano-2H-chromene, m.p. 136°–138°
2,2-dimethyl-4-(1H-2-pyridazinon-1-yl)-6-cyano-3-chromanol, m.p. 216°–218°
2,2-dimethyl-4-(4,5-dihydro-1H-6-pyridazinon-1yl)-6-cyano-2H-chromene
2,2-dimethyl-4-(4,5-dihydro-1H-6-pyridazinon-1-yl)-6-cyano-3-chromanol, m.p. 163°–164.5°
2,2-dimethyl-4-(6-hydroxy-3-pyridazinyl-oxy)-6-cyano-3-chromanol, m.p. 254°–256°
2,2-dimethyl-4-(1H-3-ethoxycarbonyl-6-pyridazinon-1-yl)-6-cyano-2H-chromene
2,2-dimethyl-4-(1H-3-ethoxycarbonyl-6-pyridazinon-1-yl)-6-cyano-3-chromanol, m.p. 259°–260.5°
2,2-dimethyl-4-(1H-2-pyrimidinon-1-yl)-6-cyano-2H-chromene
2,2-dimethyl-4-(1H-2-pyrimidinon-1-yl)-6-cyano-3-chromanol, m.p. 250°–252°
2,2-dimethyl-4-(1H-4-hydroxy-2-pyrimidinon-1-yl)-6-cyano-2H-chromene, m.p. 278°–279.5°
2,2-dimethyl-4-(1H-4-hydroxy-2-pyrimidinon-1-yl)-6-cyano-3-chromanol, no m.p. up to 300°
2,2-dimethyl-4-(1H-6-pyrimidinon-1-yl)-6-cyano-2H-chromene
2,2-dimethyl-4-(1H-6-pyrimidinon-1-yl)-6-cyano-3-chromanol, m.p. 207°–208°
2,2-dimethyl-4-(4-hydroxy-3-pyrimidinyl-oxy)-6-cyano-3-chromanol, m.p. 235°–237°
2,2-dimethyl-4-(1H-2-pyrazinon-]-yl)-d-cyano-2H-chromene, m.p. 136°–138°
2,2-dimethyl-4-(1H-2-pyrazinon-1-yl)-6-cyano-3-chromanol, m.p. 255°–257°

Example 2

A mixture of 20.1 g of IIa, 9.5 g of pyridone and 150 ml of triethylamine is heated at 110° for 2 hours, cooled, evaporated and then worked up in the customary manner. This gives "B", together with only traces of "A".

The following are obtained analogously from the corresponding 3,4-epoxychromans:
2-methyl-4-(1H-2-pyridon-1-yl)-2H-chromene
2-methyl-4-(1H-2 -pyridon-1-yl)-6-cyano-2H-chromene
2-methyl-4-(1H-2 -pyridon-1-yl)-6-nitro-2H-chromene
2-methyl-2-ethyl-4-(1H-2-pyridon-1-yl)-6-cyano-2H-chromene
2,2-diethyl-4-(1H-2-pyridon-1-yl)-6-cyano-2H-chromene
2,2-trimethylene -4-(1H-2-pyridon-1-yl)-6-cyano-2H-chromene
2,2-tetramethylene-4-(1H-2-pyridon-1-yl)-6-cyano-2H-chromene, m.p. 181°–183°
2,2-pentamethylene-4-(1H-2-pyridon-1-yl)-6-cyano-2H-chromene, m.p. 202°–204°
2,2-hexamethylene-4-(1H-2-pyridon-1-yl)-6-cyano-2H-chromene
2,2-dimethyl-4-(1H-6-methyl-2-pyridon-1-yl)-6-cyano-2H-chromene
2,2-dimethyl-4-(1H-3-fluoro-2-pyridon-1-yl)-6-cyano-2H-chromene
2,2-dimethyl-4-(1H-3,5-diiodo-2-pyridon-1-yl)-67cyano-2H-chromene
2,2-dimethyl-4-(1H-5-methoxy-2-pyridon-1-yl)-6-cyano-2H-chromene
2,2-dimethyl-4-(1H-5-methoxycarbonyl-2-piridon-1-yl)-6-cyano-2H-chromene
2,2-dimethyl-4-(1H-2-pyridon-1-yl)-2H-chromene 2,2-dimethyl-4-(1H-2-pyridon-1-yl)-6-methyl-2H-chromene 2,2-dimethyl-4-(1H-2-pyridon-1-yl)-6-methoxy-2H-chromene 2,2-dimethyl-4-(1H-2-pyridon-1-yl)-6-thioacetyl-2H-chromene 2,2-dimethyl-4-(1H-2-pyridon-1-yl)-6-methoxythiocarbonyl-2H-chromene 2,2-dimethyl-4-(1H-2-pyridon-1-yl)-6-thio(no)acetoxy-2H-chromene 2,2-dimethyl-4-(1H-2-pyridon-1-yl)-6-hydroxymethyl-2H-chromene 2,2-dimethyl-4-(1H-2-pyridon-1-yl)-6-dimethylamino-2H-chromene 2,2-dimethyl-4-(1H-2-pyridon-1-yl)-6-bromo-2H-chromene 2,2-dimethyl-4-(1H-2-pyridon-1-yl)-6-iodo-2H-chromene 2,2-dimethyl-4-(1H-2-pyridon-1-yl)-6-methylsulfinyl-2H-chromene 2,2-dimethyl-4-(1H-2-pyridon-1-yl)-6-methylsulfonyl-2H-chromene

Example 3

A mixture of 2 g of IIa and 1 g of pyridone is heated at 110° for 2 hours and cooled, and the residue is worked up in the customary manner. This gives "B", together with only traces of "A".

Example 4

A mixture of 2 g of IIa, 1.17 g of pyridone Na salt and 30 ml of ethanol is boiled for 3 hours. Working up analogously to Example 1 gives "A" and "B" in a ratio of approx. 3:2.

Example 5

A solution of 2 g of IIa and 1.1Z g of pyridone Na salt in 30 ml of ethanol is allowed to stand at 20° for 16 hours. This gives "B", together with only traces of "A".

Example 6

A solution of 2 g of IIa and 1.17 g of pyridone Na salt in 30 ml of ethanol and 2 ml of pyridine is boiled for 1.5 hours and cooled; the "B" which has been precipitated is filtered off. Only traces of "A" are formed.

Example 7

0.4 g of a 60i dispersion of NaH in oil is added with stirring to a solution of 2.82 g of trans-2,2-dimethyl-3-bromo-6-cyanochroman-4-ol in 15 ml of DMSO. The mixture is stirred for I hour, 2,2-dimethyl-3,4-epoxy-6-cyanochroman being formed as an intermediate. 1.43 g of 1H-2-pyridone and a further 0.5 g of the NaH dispersion are added and the mixture is stirred for 16 hours at 20°. Working up analogously to Example 1 gives "A" (m.p. 146°–148°) and "B" (m.p. 244°).

Example 8

96 mg of 80% NaH in paraffin oil are added to a solution of 1 g of "B" in 30 ml of DMSO and the mixture is allowed to stand at 20° for 16 hours, Working up in the customary manner gives "A", m.p. 146°–148°.

Example 9

A mixture of 2 g of "B" 11.7 ml of formic acid and 3.3 ml of acetic anhydride is allowed to stand for 16 hours at 20° and is then heated at 40°–42° for 2 hours. Evaporation and working up in the customary manner gives 2,2-dimethyl-3-formyloxy-4-(1H-2-pyridon-1-yl)-6-cyanochroman, m.p. 203.5°–204°.

The following is obtained analogously from the corresponding 3-hydroxy-chroman:

2,2-dimethyl-3-formyloxy-4-(1H-2-pyridon-1-yl)-6-nitrochroman, m.p. 188°–193°.

Example 10

A mixture of 1 g of "B" and 5 ml of acetic anhydride is boiled for 1 hour. The mixture is cooled and worked up in the customary manner to give 2,2-dimethyl-3-acetoxy-4-(1H-2-pyridon-1-yl)-6-cyanochroman, m.p. 228°–228.5°.

Example 11

2.96 g of "B" are suspended in 100 ml of water, and 3.2 g of bromine are added dropwise, with stirring, at 10°–20°. The substance dissolves and 2,2-dimethyl-4-(1H-3,5-dibromo-2-pyridon-1-yl)-6-cyanochroman-3-ol is precipitated and is filtered off, m.p. 207°–209°.

Example 12

2.78 g of "A" are dissolved in a mixture of 10 ml of concentrated nitric acid (68%; D=1.41) and 12 ml of concentrated sulfuric acid, the mixture is stirred for 3 hours at 20° and is poured onto ice; filtering off the product and washing it with water gives a mixture of 2,2-dimethyl-4-(1H-3-nitropyridon-1-yl)-6-cyano-2H-chromene and 2,2-dimethyl-4-(1H-5-nitropyridon-1-yl)-6-cyano-2H-chromene in the ratio of approx. 1:3, which can be separated by chromatography.

Example 13

A solution of 1 g of 2,2-dimethyl-4-(1H-3-nitro-2-pyridon-1-yl)-6-methoxycarbonylchroman-3-ol in 25 ml of methanol is hydrogenated at 20° and 1 bar over 0.5 g of 5% Pd-on-C until absorption ceases. The mixture is filtered and the filtrate is evaporated to give 2,2-dimethyl-4-(1H-3-amino-2-pyridon-1-yl)-6-methoxycarbonylchroman-3-ol.

Example 14

A solution of 1 g of 2,2-dimethyl-4-(1H-3-amino-2-pyridon-1-yl)-6-cyano-2H-chromene in 15 ml of HCOOH and 1 ml of pyridine is boiled for 19 hours and evaporated. Working up in the customary manner gives 2,2-dimethyl-4-(1H-3-formamido-2-pyridon-1-yl)-6-cyano-2H-chromene.

Example 15

A mixture of 1 g of 2,2-dimethyl-4-(1H-5-amino-2-pyridon-1-yl)-6-cyano-2H-chromene, 10 ml of acetic anhydride and 10 ml of pyridine is allowed to stand at 20° for 16 hours. The mixture is evaporated and the product is purified by chromatography to give 2,2-dimethyl-4-(1H-5-acetamido-2-pyridon-1-yl)-6-cyano-2H-chromene.

Example 16

HCl is passed, with stirring, into a boiling solution of 1 g of "A" in 50 ml of methanol and 2 ml of water for 14 hours. The mixture is allowed to cool and to stand overnight. The precipitated 2,2-dimethyl-4-(1H-2-pyridon-1-yl)-2H-chromene-6-carboxylic acid is filtered off, m.p. 281°–284°.

Example 17

A mixture of 2.78 g of "A", 31 g of Na$_3$PO$_4$.12 H$_2$O, 28 ml of pyridine, 28 ml of water, 67 ml of acetic acid and 25 of Raney Ni (moist with water) is stirred for 3 hours at 20°. The mixture is filtered and worked up in the customary manner to give 2,2-dimethyl-4-(1H-2-pyridon-1-yl)-6-formyl-2H-chromene, m.p. 160°–162°.

The following are obtained analogously:
2,2-dimethyl-4-(1H-2-pyridon-1-yl)-6-formylchroman-3-ol, m.p. 210°–214°
2,2-dimethyl-4-(1H-2-pyridon-1-yl)-7-formyl-2H-chromene
2,2-dimethyl-4-(1H-2-pyridon-1-yl)-7-formyl-chroman-3-ol.

Example 18

2.78 g of "A" are dissolved in 40 ml of tert.-butanol and 5.6 g of powdered KOH are added with stirring. Boiling for 1 hour and working up in the customary manner gives 2,2-dimethyl-4-(1H-2-pyridon-1-yl)-6-carbamoyl-2H-chromene m.p. 250°–252°.

The following are obtained analogously:
2,2-dimethyl-4-(1H-2-pyridon-1-yl)-6-carbamoyl-chroman-3-ol
2,2-dimethyl-4-(1H-2-pyridon-1-yl)-7-carbamoyl-2H-chromene
2,2-dimethyl-4-(1H-2-pyridon-1-yl)-7-carbamoyl-chroman-3-ol.

Example 19

H$_2$S is passed at 20° for 5 hours into a solution of 2.78 g of "A" in a mixture of 20 ml of pyridine and 10 ml of triethylamine; the mixture is evaporated and worked up in the customary manner to give 2,2-dimethyl-4-(1H-2-pyridon-1-yl)-6-thiocarbamoyl-2H-chromene, m.p. 254°–257°.

The following are obtained analogously:
2,2-dimethyl-4-(1H-2-pyridon-1-yl)-6-thiocarbamoyl-chroman-3-ol, m.p. 228°.
2,2-dimethyl-4-(1H-2-pyridon-1-yl)-7-thiocarbamoyl-2H-chromene
2,2-dimethyl-4-(1H-2-pyridon-1-yl)-7-thiocarbamoyl-chroman-3-ol

Example 20

A mixture or 296 mg of "B", 808 mg of Lawesson reagent and 50 ml of toluene is boiled for I hour under N$_2$. Working up in the customary manner gives 2,2-dimethyl-4-(1H-2-thiopyridon-1-yl)-6-cyanochroman-3-ol.

2,2-Dimethyl-4-(1H-2-thiopyridon-1-yl)-6-cyano-2H-chromene is obtained analogously from "A".

Example 21

Analogously to Example 1, there is obtained:
2,2-dimethyl-4-(1H-4-methoxy-2-pyridon-1-yl)-6-cyano-2H-chromene, m.p. 92°–95°
2,2-dimethyl-4-(1H-4-methoxy-2-pyridon-1-yl)-6-cyanochroman-3-ol, m.p. 228°–230°
2,2-dimethyl-4-(1H-4-ethoxy-2-pyridon-1-yl)-6-cyano-2H-chromene, m.p. 102°–104°
2,2-dimethyl-4-(1H-4-ethoxy-2-pyridon-1-yl)-6-cyanochroman-3-ol, m.p. 210°–212°
2,2-dimethyl-4-(1H-4-acetoxy-2-pyridon-1-yl)-6-cyano-2H-chromene, m.p. 170°–172°
2,2-dimethyl-4-(1H-4-acetoxy-2-pyridon-1-yl)-6-cyanochroman-3-ol
2,2-dimethyl-4-(1H-2-pyridon-1-yl)-6-cyan-8-nitro-2H-chromene, m.p. 149°–151°
2,2-dimethyl-4-(1H-2-pyridon-1-yl)-6-cyan-8-nitrochroman-3-ol
2,2-dimethyl-4-(1H-2-pyridon-1-yl)-6-hydroxymethyl-2H-chromene
2,2-dimethyl-4-(1H-2-pyridon-1-yl)-6-hydroxymethylchroman-3-ol, m.p. 170°–172°
2,2-tetramethylene-4-(1H-2-pyridon-1-yl)-6-nitro-2H-chromene, m.p. 229°–230°
2,2-tetramethylene-4-(1H-2-pyridon-1-yl)-6-nitrochroman-3-ol, m.p. 249°
2,2-pentamethylene-4-(1H-2-pyridon-1-yl)-6-nitro-2H-chromene, m.p. 210°–212°
2,2-pentamethylene-4-(1H-2-pyridon-1-yl)-6-nitrochroman-3-ol, m.p. 247°
2,2-dimethyl-4-(1H-3-methoxy-6-pyridazinon-1-yl)-6-cyano-2H-chromene
2,2-dimethyl-4-(1H-3-methoxy-6-pyridazinon-1-yl)-6-cyanochroman-3-ol, m.p. 165°–167°.

Example 22

Analogously to Example 1, there are obtained from IIa:

with 1H-3-hydroxy-2-pyridone (=2,3-dihydroxypyridine): 2,2-dimethyl-4-(2-hydroxy-3-pyridyl-oxy)-6-cyano-3-chromanol, m.p. 262°–265°;

with 1H-4-hydroxy-2-pyridone (=2,4-dihydroxypyridine): 2,2-dimethyl-4-(2-hydroxy-4-pyridyl-oxy)-6-cyano-3-chromanol, m.p. 248°–250°;

with 1H-5-hydroxy-2-pyridone (=2,5-dihydroxypyridine): 2,2-dimethyl-4-(2-hydroxy-5-pyridyl-oxy)-6-cyano-3-chromanol, m.p. 256.5°–258°;

with 1H-3-hydroxy-6-pyridazinone (=3,6-dihydroxypyridine): 2,2-dimethyl-4- (6-hydroxy-3-pyridazinyl-oxy) -6-cyano-3-chromanol. m.p. 254°–256°;

with 1H-4-hydroxy-6-pyrimidinone (=4, 6-dihydroxypyrimidine): 2,2-dimethyl-4-(4-hydroxy-3-pyrimidinyl-oxy)-6-cyano-3-chromanol, m.p. 235°–237°.

Example 23

A mixture of 30 g of IIa, 22 g of pyridone, 10 ml of pyridine and 100 ml of ethanol is refluxed for 2 hours. After cooling, the precipitated "B" is collected by filtration.

Example 24

"B" (100 g) and NaOH on a carrier (0.8–1.6 mm, ~14–25 mesh ASTM; Cat. No. 1567, E. Merck) are refluxed in dioxane (3 l) in a stream of N$_2$ for 10 min. The solution is filtered and evaporated, and the residue is dissolved in CH$_2$Cl$_2$ (1 l ) and washed twice with water. The organic phase is dried and evaporated and the obtained "A" is recrystallized from diisopropyl ether.

Example 25

A mixture of 275 g (−)-enantiomer of IIa, 187.5 g of pyridone, 140 ml of Triton B and 4200 ml of ethanol is refluxed until the solution has become clear. The solution is cooled to 20°, seeded with 100 mg of (−)-(3S,4R)-2,2-dimethyl-4-(1H-2-pyridon-1-yl)-6-cyanochroman-3-ol ["(−)−B"] and stirred for 48 hours at 20°. The precipitate of "(−)-B" is filtered and washed with hexane: m.p. 262°–263°; α−88.5°.

"(−)-B" is also preferably prepared in accordance with U.S. Pat. No.4,952,696, whose disclosure is entirely incorporated by reference herein.

Example 26

A mixture of 20.1 g of IIa, 11.2 g of 3,6-dihydroxy-pyridazine, 8 ml of pyridine and 400 ml of ethanol is refluxed for 7 hours. The solution is evaporated and the residue chromatographed on silicagel (CH$_2$CL$_2$→ethyl acetate→20% methanol/ethyl acetate as a gradient solution). The homogeneous fractions are combined to give 2,2-dimethyl-4-(6-hydroxy-3-pyridazinyl-oxy)-6-cyano-3-chromanol, m.p. 254°–256°.

Example 27

A mixture of 21.5 g of 2,2,3-trimethyl-3,4-epoxy-6-cyanochroman ("IIb"), 9.5 g of 1H-2-pyridone ("pyridone"), 3 g of an 80% dispersion of NaH in paraffin oil and 600 ml of DMSO is stirred at 20° for 16 hours and poured into water, and the mixture is extracted using ethyl acetate. The extract is evaporated and the residue is chromatographed on silica gel. 2,2,3-Trimethyl-4-(1H-2-pyridon-1-yl)-6-cyano-2H-chromene ("C"; m.p. 212°) is eluted using dichloromethane, then 2,2,3-trimethyl-4-(1H-2-pyridon-1-yl)-6-cyano-chroman-3-ol ("D"; m.p. 185°–186°) using ethyl acetate.

Preparation of the starting material:

(a) A mixture of 81 g of 3-acetyl-4-hydroxybenzonitrile, 48 ml of acetone, 11.8 ml of pyrrolidine and 300 ml of toluene is allowed to stand at 20° for 1 hour, then boiled for 2 hours in a water separator and cooled. After customary working up, 2,2-dimethyl-6-cyano-4-chromanone is obtained, m.p. 119°–120°.

A solution of 24 g of the chromanone, 12 g of paraformaldehyde and 24 ml of piperidine in 300 ml of ethanol is heated at 70° for 3 hours and evaporated. The residue is taken up in dichloromethane/petroleum ether 1:1, the mixture is filtered through silica gel and evaporated, and 2,2-dimethyl-3-methylene-6-cyano-4-chromanone is obtained as an unstable oil.

6 g of NaBH$_4$ are added to a solution of 25 g of the above chromanone in 500 ml of methanol, and the mixture is stirred at 20° for 1 hour and evaporated. After customary working up, 2,2,3-trimethyl-6-cyano-4-chromanol is obtained as an oily isomer mixture.

(d) A solution of 27 g of the above mixture and 1.2 g of p-toluenesulfonic acid in 400 ml of toluene is boiled in a water separator for 3 hours. The mixture is evaporated, the residue is dissolved in dichloromethane/petroleum ether 1:1, the solution is filtered through silica gel and evaporated again, and 2,2,3-trimethyl-6-cyano-2H-chromene is obtained, m.p. 55°.

(e) A solution of 6.4 g of m-chloroperbenzoic acid in 40 ml of dichloromethane is added dropwise with stirring to a solution of 6.8 g of the above chromene in 100 ml of dichloromethane. The mixture is stirred for 16 hours, filtered, dilute sodium hydroxide solution is added, and the mixture is worked up as usual and 2,2,3-trimethyl-i,4-epoxy-6cyanochroman (IIb) is obtained, m.p. 118°.

The enantiomers of IIb are obtainable by reaction of 2,2,3-trimethyl-6-cyano-2H-chromene with N-bromosuccinimide to yield 2,2,3-trimethyl-3-bromo-6-cyano-chroman-4-ol, esterification with (+)- or (−)-camphanic acid chloride to give the diastereomeric camphanic acid esters, separation of the enantiomers by crystallization or chromatography and treatment with base, thereby effecting saponification and cyclization to the enantiomeric epoxide IIb.

The following are obtained analogously:

2,2,3-trimethyl-4-(1H-2-thiopyridon-1-yl )-6-cyano-2H-chromene 2,2,3-trimethyl-4-(1H-2-thiopyridon-1-yl)-6-cyano-chroman-3-ol
2,2,3-trimethyl-4-(1H-3-chloro-2-pyridon-1-yl)-6-cyano-2H-chromene
2,2,3-trimethyl-4-(1H-3-chloro-2-pyridon-1-yl)-6-cyanochroman-3-ol
2,2,3-trimethyl-4-(1H-5-chloro-2-pyridon-1-yl)-6-cyano-2H-chromene
2,2,3-trimethyl-4-(1H-5-chloro-2-pyridon-1-yl)-6-cyanochroman-3-ol
2,2,3-trimethyl-4-(1H-6-chloro-2-pyridon-1-yl)-6-cyano-2H-chromene
2,2,3-trimethyl-4-(1H-6-chloro-2-pyridon-1-yl)-6-cyanochroman-3-ol
2,2,3-trimethyl-4-(1H-3-hydroxy-2-pyridon-1-yl)-6-cyano-2H-chromene
2,2,3-trimethyl-4-(1H-3-hydroxy-2-pyridon-1-yl)-6-cyanochroman-3-ol
2,2,3-trimethyl-4-(1H-4-hydroxy-2-pyridon-1-yl)-6-cyano-2H-chromene
2,2,3-trimethyl-4-(1H-4-hydroxy-2-pyridon-1-yl)-6-cyanochroman-3-ol
2,2,3-trimethyl-4-(1H-5-hydroxy-2-pyridon-1-yl)-6-cyano-2H-chromene
2,2,3-trimethyl-4-(1H-5-hydroxy-2-pyridon-1-yl)-6-cyanochroman-3-ol
2,2,3-trimethyl-4-(1H-3-methoxy-2-pyridon-1-yl)-6-cyano-2H-chromene
2,2,3-trimethyl-4-(1H-3-methoxy-2-pyridon-1-yl)-6-cyanochroman-3-ol
2,2,3-trimethyl-4-(1H-3-acetoxy-2-pyr-idon-1-yl)-6-cyano-2H-chromene
2,2,3-trimethyl-4-(1H-3-acetoxy-2 -pyridon- 1-yl)-6-cyanochroman-3-ol
2,2,3-trimethyl-4-(1H-3-nitro-2-pyridon-1-yl)-6-cyano-2H-chromene
2,2,3-trimethyl-4- (1H-3-nitro-2-pyridon-1-yl)-6-cyanochroman-3-ol
2,2,3-trimethyl-4-(1H-5-nitro-2-pyridon-1-yl)-6-cyano-2H-chromene
2,2,3-trimethyl-4-(1H-5-nitro-2-pyridon-1-yl)-6-cyanochroman-3-ol
2,2,3-trimethyl-4-(1H-3-amino-2-pyridon-1-yl)-6-cyano-2H-chromene
2,2,3-trimethyl-4-(1H-3-amino-2-pyridon-1-yl)-6-cyanochroman-3-ol
2,2,3-trimethyl-4-(1H-5-amino-2-pyridon-1-yl)-6-cyano-2H-chromene
2,2,3-trimethyl-4-(1H-5-amino-2-pyridon- 1-yl)-6-cyanochroman-3-ol
2,2,3-trimethyl-4-(1H-3-acetamido-2-pyridon-1-yl)-6-cyano-2H-chromene
2,2,3-trimethyl-4-(1H-3-acetamido-2-pyridon-1-yl)-6-cyano-chroman-3-ol
2,2,3-trimethyl-4-(1H-5-acetamido-2-pyridon-1-yl)-6-cyano-2H-chromene
2,2,3-trimethyl-4-(1H-5-acetamido-2-pyridon-1-yl)-6-cyano-2H-chromene
2,2,3-trimethyl-4-(1H-3-carboxy-2-pyridon-1-yl)-6-cyano-2H-chromene
2,2,3-trimethyl-4-(1H-3-carboxy-2-piridon-1-yl)-6-cyanochroman-3-ol
2,2,3-trimethyl-4-(1H-5-carboxy-2-pyridon-1-yl)-6-cyano-2H-chromene
2,2,3-trimethyl-4-(1H-5-carboxy-2-pyridon- 1-yl)-6-cyanochroman-3-ol 2,2,3-trimethyl-4-(1H-3,5-dichloro-2-pyridon-1-yl)-6-cyano-2H-chromene
2,2,3-trimethyl-4-(1H-3,5-dichloro-2-pyridon-1-yl)-6-cyanochroman-3-ol
2,2,3-trimethyl-4-(1H-3,5-dibromo-2-pyridon-1-yl)-6-cyano-2H-chromene
2,2,3-trimethyl-4-(1H-3,5-dibromo-2-pyridon-1-yl)-6-cyanochroman-3-ol
2,2,3-trimethyl-4-(1H-3-chloro-5-nitro-2-pyridon-1-yl)-6-cyano-2H-chromene
2,2,3-trimethyl-4-(1H-3-chloro-5-nitro-2-pyridon-1-yl)-6-cyano-chroman-3-ol
2,2,3-trimethyl-4-(1H-3-nitro-5-chloro-2-pyridon-1-yl)-6-cyano-2H-chromene
2,2,3-trimethyl-4-(1H-3-nitro-5-chloro-2-pyridon-1-yl)-6-cyano-chroman-3-ol
2,2,3-trimethyl-4-(1H-3-bromo-5-nitro-2-pyridon-1-yl)-6-cyano-2H-chromene
2,2,3-trimethyl-4-(1H-3-bromo-5-nitro-2-pyridon-1-yl)-6-cyanochroman-3-ol
2,2,3-trimethyl-4-(1H-3-nitro-5-bromo-2-pyridon-1-yl)-6-cyano-2H-chromene
2,2,3-trimethyl-4-(1H-3-nitro-5-bromo-2-pyridon-1-yl)-6-cyano-chroman-3-ol
2,2,3-trimethyl-4-(1H-3,5-dinitro-2-pyridon-1-yl)-6-cyano-2H-chromene
2,2,3-trimethyl-4-(1H-3,5-dinitro-2-pyridon-1-yl)-6-cyano-chroman-3-ol
2,2,3-trimethyl-4-(1H-3-chloro-5-amino-2-pyridon-1-yl)-6-cyano-2H-chromene
2,2,3-trimethyl-4-(1H-3-chloro-5-amino-2-pyridon-1-yl)-6-cyano-chroman-3-ol
2,2,3-trimethyl-4-(1H-3-amino-5-chloro-2-pyridon-1-yl)-6-cyano-2H-chromene
2,2,3-trimethyl-4-(1H-3-amino-5-chloro-2-pyridon-1-yl)-6-cyano-chroman-3-ol
2,2,3-trimethyl-4-(1H-3-bromo-5-amino-2-pyridon-1-yl)-6-cyano-2H-chromene
2,2,3-trimethyl-4-(1H-3-bromo-5-amino-2-pyridon-1-yl)-6-cyano-chroman-3-ol
2,2,3-trimethyl-4-(1H-3-amino-5-bromo-2-pyridon-1-yl)-6-cyano-2H-chromene
2,2,3-trimethyl-4-(1H-3-amino-5-bromo-2-pyridon-1-yl)-6-cyanochroman-3-ol
2,2,3-trimethyl-4-(1H-3-chloro-5-acetamido-2-pyridon-1-yl)-1-yl)-6-cyano-2H-chromene
2,2,3-trimethyl-4-(1H-3-chloro-5-acetamido-2-pyridon-1-yl)-6-cyano-chroman-3-ol
2,2,3-trimethyl-4-(1H-3-acetamido-5-chloro-2-pyridon-1-yl)-6-cyano-2H-chromene
2,2,3-trimethyl-4-(1H-3-acetamido-5-chloro-2-pyridon-1-yl)-6-cyano-chroman-3-ol
2,2,3-trimethyl-4-(1H-3-bromo-5-acetamido-2-pyridon-1-yl)-6-cyano-2H-chromene
2,2,3-trimethyl-4-(1H-3-bromo-5-acetamido-2-pyridon-1yl)-6-cyano-chroman-3-ol
2,2,3-trimethyl-4-(1H-3-acetamido-5-bromo-2-pyridon-1yl)-6-cyano-2H-chromene
2,2,3-trimethyl-4-(1H-3-acetamido-5-bromo-2-pyridon-1yl)-6-cyano-chroman-3-ol
2,2,3-trimethyl-4-(1H-2-pyridon-1-yl)-6-nitro-2H-chromene
2,2,3-trimethyl-4-(1H-2-pyridon-1-yl)-6-nitro-chroman-3-ol, m.p. 220°–222°
2,2,3-trimethyl-4-(1H-2-thiopyridon-1-yl)-6-nitro-2H-chromene
2,2,3-trimethyl-4-(1H-2-thiopyridon-1-yl)-6-nitro-chroman-3-ol
2,2,3-trimethyl-4-(1H-3-chloro-2-pyridonil-yl)-6-nitrochromene
2,2,3-trimethyl-4-(1H-3-chloro-2-pyridon-1-yl)-6-nitrochroman-3-ol
2,2,3-trimethyl-4-(1H-5-chloro-2-pyridon-1-yl-)-6-nitro-2H-chromene
2,2,3-trimethyl-4-(1H-5-chloro-2-pyridon-1-yl)-6-nitrochroman-3-ol
2,2,3-trimethyl-4-(1H-6-chloro-2-pyridon-1-yl)-6-nitro-2H-chromene
2,2,3-trimethyl-4-(1H-6-chloro-2-pyridon-1-yl)-6-nitrochroman-3-ol
2,2,3-trimethyl-4-(1H-3-hydroxy-2-pyridon-1-yl)-6-nitro-2H-chromene
2,2,3-trimethyl-4-(1H-3-hydroxy-2-pyridon-1-yl)-6-nitrochroman-3-ol
2,2,3-trimethyl-4-(1H-4-hydroxy-2-pyridon-1-yl)-6-nitro-2H-chromene
2,2,3-trimethyl-4-(1H-4-hydroxy-2-pyridon-1-yl)-6-nitrochroman-3-ol
2,2,3-trimethyl-4-(1H-5-hydroxy-2-pyridon-1-yl)-6-nitro2H-chromene
2,2,3-trimethyl-4-(1H-5-hydroxy-2-pyridon-1-yl)-6-nitrochroman-3-ol
2,2,3-trimethyl-4-(1H-3-methoxy-2-pyridon-1-yl)-6-nitro-2H-chromene
2,2,3-trimethyl-4-(1H-3-methoxy-2-pyridon-1-yl)-6-nitrochroman-3-ol
2,2,3-trimethyl-4-(1H-3-acetoxy-2-pyridon-1-yl)-6-nitro-2H-chromene
2,2,3-trimethyl-4-(1H-3-acetoxy-2-pyridon-1-yl)-6-nitrochroman-3-ol
2,2,3-trimethyl-4-(1H-3-nitro-2-pyridon-1-yl)-6-nitro-2H-chromene
2,2,3-trimethyl-4-(1H-3-nitro-2-pyridon-1-yl)-6-nitro-chroman-3-ol
2,2,3-trimethyl-4-(1H-5-nitro-2-pyridon-1-yl)-6-nitro-2H-chromene
2,2,3-trimethyl-4-(1H-5-nitro-2-pyridon-1-yl)-6-nitro-chroman-3-ol
2,2,3-trimethyl-4-(1H-3-amino-2-pyridon-1-yl)-6-nitro-2H-chromene
2,2,3-trimethyl-4-(1H-3-amino-2-pyridon-1-yl)-6-nitrochroman-3-ol
2,2,3-trimethyl-4-(1H-5-amino-2-pyridon-1-yl)-6-nitro-2H-chromene
2,2,3-trimethyl-4-(1H-5-amino-2-pyridon-1-yl)-6-nitrochroman-3-ol
2,2,3-trimethyl-4-(1H-3-acetamido-2-pyridon-1-yl)-6-nitro-2H-chromene
2,2,3-trimethyl-4-(1H-3-acetamido-2-pyridon-1-yl)-6-nitro-chroman-3-ol
2,2,3-trimethyl-4-(1H-5-acetamido-2-pyridon-1-yl)-6-nitro-2H-chromene
2,2,3-trimethyl-4-(1H-5-acetamido-2-pyridon-1-yl)-6-nitrochroman-3-ol
2,2,3-trimethyl-4-(1H-3-carboxy-2-pyridon-1-yl)-6-nitro-2H-chromene
2,2,3-trimethyl-4-(1H-3-carboxy-2-pyridon-1-yl)-6-nitrochroman-3-ol
2,2,3-trimethyl-4-(1H-5-carboxy-2-pyridon-1-yl)-6-nitro-2H-chromene
2,2,3-trimethyl-4-(1H-5-carboxy-2-pyridon-1-yl)-6-nitrochroman-3-ol
2,2,3-trimethyl-4-(1H-3,5-dichloro-2-pyridon-1-yl)-6-nitro-2H-chromene
2,2,3-trimethyl-4-(1H-3,5-dichloro-2-pyridon-1-yl)-6-nitrochroman-3-ol 2,2,3-trimethyl-4-(1H-3,5-dibromo-2-pyridon-1-yl)-6-nitro-2H-chromene 2,2,3-trimethyl-4-(1H-3,5-dibromo-2-pyridon-1-yl)-6-nitro-chroman-3-ol 2,2,3-trimethyl-4-(1H-3-chloro-5-nitro-2-pyridon-1-yl)-6-nitro-2H-chromene 2,2,3-trimethyl-4-(1H-3-chloro-5-nitro-2-pyridon-1-yl)-6-nitro-chroman-3-ol 2,2,3-trimethyl-4-(1H-3-nitro-5-chloro-2-pyridon-1-yl)-6-nitro-2H-chromene 2,2,3 - trimethyl-4-(1H-3-nitro-5-chloro-2-pyridon-1-yl)-6-nitro-chroman-3-ol 2,2,3-trimethyl-4-(1H-3-bromo-5-nitro-2-pyridon-1-yl)-6-nitro-2H-chromene 2,2,3-trimethyl-4-(1H-3-bromo-5-nitro-2-pyridon-1-yl)-6-nitrochroman-3-ol 2,2,3-trimethyl-4-(1H-3-nitro-5-bromo-2-pyridon-1-yl)-6-nitro-2H-chromene 2,2,3 -trimethyl-4-(1H-3-nitro-5-bromo-2-pyridon-1-yl)-6-nitro-chroman-3-ol 2,2,3-trimethyl-4-(1H-3,5-dinitro-2-pyridon-1-yl)-6-nitro-2H-chromene 2,2,3-trimethyl-4-(1H-3,5-dinitro-2-pyridon-1-yl)-6-nitro-chroman-3-ol 2,2,3-trimethyl-4-(1H-3-chloro-5-amino-2-pyridon-1-yl)-6-nitro-2H-chromene 2,2,3-trimethyl-4-(1H-3-chloro-5-amino-2-pyridon-1-yl)-6-nitro-chroman-3-ol 2,2,3-trimethyl-4-(1H-3-amino-5-chloro-2-pyridon-1-yl )-6-nitro-2H-chromene 2,2,3-trimethyl-4-(1H-3-amino-5-chloro-2-pyridon-1-yl)-6-nitro-chroman-3-ol 2,2,3-trimethyl-4-(1H-3-bromo-5-amino-2-pyridon-1-yl)-6-nitro- 2H-chromene 2,2,3-trimethyl-4-(1H-3-bromo-5-amino-2-pyridon-1-yl)-6-nitro-chroman-3-ol 2,2,3-trimethyl-4-(1H-3-amino-5-bromo-2-pyridon-1-yl)-6-nitro-2H-chromene 2,2,3-trimethyl-4-(1H-3-amino-5-bromo-2-pyridon-1-yl)-6-nitro-chroman-3-ol 2,2,3-trimethyl-4-(1H-3-chloro-5-acetamido-2-pyridon-1yl)-6-nitro-2H-chromene 2,2,3-trimethyl-4-(1H-3-chloro-5-acetamido-2-pyridon-1yl)-6-nitro-chroman-3-ol 2,2,3-trimethyl-4-(1H-3-acetamido-5-chloro-2-pyridon-1yl)-6-nitro-2H-chromene 2,2,3-trimethyl-4-(1H-3-acetamido-5-chloro-2-pyridon-1yl)-6-nitro-chroman-3-ol 2,2,3-trimethyl-4-(1H-3-bromo-5-acetamido-2-pyridon-1yl)-6-nitro-2H-chromene 2,2,3-trimethyl-4-(1H-3-bromo-5-acetamido-2-pyridon-1yl)-6-nitro-chroman-3-ol 2,2,3-trimethyl-4-(1H-3-acetamido-5-bromo-2-pyridon-1yl)-6-nitro-2H-chromene 2,2,3-trimethyl-4-(1H-3-acetamido-5-bromo-2-pyridon-1yl)-6-nitro -chroman-3-ol 2,2,3-trimethyl-4-(1H-2-pyridon-1-yl)-6 -acetyl-2H-chromene 2,3-trimethyl-4-(1H-2-pyridon-1-yl)-6-acetyl-chroman-3-ol 2,2,3-trimethyl-4-(1H-2-pyridon-1-yl)-6-methoxycarbonyl-2H-chromene 2,2,3-trimethyl-4-(1H-2-pyridon-1-yl)-6-methoxycarbonylchroman-3-ol 2,2,3-trimethyl-4-(1H-2-pyridon-1-yl)-6-ethoxycarbonyl-2H-chromene 2,2,3-trimethyl-4-(1H-2-pyridon-1-yl)-6-ethoxycarbonylchroman-3-ol 2,2,3-trimethyl-4-(1H-2-pyridon-1-yl)-6-fluoro-2H-chromene 2,2,3-trimethyl-4-(1H-2-pyridon-1-yl)-6-fluoro-chroman-3-ol 2,2,3-trimethyl-4-(1H-2-pyridon-1-yl)-6-chloro-2H-chromene 2,2,3-trimethyl-4-(1H-2-pyridon-1-yl)-6-chloro-chroman-3-ol 2,2,3-trimethyl-4-(1H-2-pyridon-1-yl)-6-trifluoromethyl-2H-chromene 2,2,3-trimethyl-4-(1H-2-pyridon-1-yl)-6-trifluoromethylchroman-3 -ol 2,2,3-trimethyl-4-(1H-2-pyridon-1-yl)-6-acetamido-2H-chromene 2,2,3-trimethyl-4-(1H-2-pyridon-1-yl)-6-acetamido-chroman-3-ol 2,2,3-trimethyl-4-(1H-2-pyridon-1-yl)-6-carbamoyl-2H-chromene 2,2,3-trimethyl-4-(1H-2-pyridon-1-yl)-6-carbamoyl-chroman-3-ol 2,2,3-trimethyl-4-(1H-2-pyridon-1-yl)-6-thiocarbamoyl-2H-chromene 2,2,3-trimethyl-4-(1H-2-pyridon-1-yl)-6-thiocarbamoylchroman-3-ol 2,2,3-trimethyl-4-(1H-2-pyridon-1-yl)-7-cyano-2H-chromene 2,2,3-trimethyl-4-(1H-2-pyridon-1-yl)-7-cyano-chroman-3-ol 2,2,3-trimethyl-4-(1H-2-pyridon-1-yl)-6-acetamido-7-nitro-2H-chromene 2,2,3-trimethyl-4-(1H-2-pyridon-1-yl)-6-acetamido-7-nitro-chroman-3-ol 2,2,3-trimethyl-4-(1H-3-nitro-2-pyridon-1-yl)-6-methoxycarbonyl-2H-chromene 2,2,3-trimethyl-4-(1H-3-nitro-2-pyridon-1-yl)-6-methoxycarbonyl-chroman-3-ol 2,2-tetramethylene-3-methyl-4-(1H-2-pyridon-1-yl)-6-cyano-2H-chromene 2,2-tetramethylene-3-methyl-4-(1H-2-pyridon-1-yl)-6-cyano-chroman-3-ol 2,2-pentamethylene-3-methyl-4-(1H-2-pyridon-1-yl)-6-cyano-2H-chromene 2,2 -pentamethylene-3-methyl-4-(1H-2-pyridon-1-yl)-6-cyano-chroman-3-ol m.p. 204°–206°

2,2,3-trimethyl-4-(1H-6-pyridazinon-1-yl)-6-cyano-2H-chromene 2,2,3-trimethyl-4-(1H-6-pyridazinon-1-yl)-6-cyano-chroman-3-ol 2,2,3-trimethyl-4-(4,5-dihydro-1H-6-pyridazinon-1-yl)-6-cyano-2H-chromene 2,2,3-trimethyl-4-(4,5-dihydro-1H-6-pyridazinon-1-yl)-6-cyano-chroman-3-ol 2,2,3-trimethyl-4-(1H-3-hydroxy-6-pyridazinon-1-yl)-6-cyano-2H-chromene 2,2,3-trimethyl-4-(1H-3-hydroxy-6-pyridazinon-1-yl)-6-cyano-chroman-3-ol 2,2,3-trimethyl-4-(1H-3-amino-6-pyridazinon-1-yl)-6-cyano-chroman-3-ol, m.p. 239°–242°

2,2,3-trimethyl-4-(1H-3-ethoxycarbonyl-6-pyridazinon-1yl)-6-cyano-chroman-3-ol 2,2,3-trimethyl-4-(1H-2-pyrimidinon-1-yl)-6-cyano-2H-chromene 2,2,3-trimethyl-4-(1H-2-pyrimidinon-1-yl)-6 -cyano-chroman-3-ol 2,2,3-trimethyl-4-(1H-4-hydroxy-2-pyrimidinon-1-yl)-6-cyano-2H-chromene 2,2,3 -trimethyl-4-(1H-4-hydroxy-2-pyrimidinon-1-yl)-6-cyano-chroman-3-ol 2,2,3-trimethyl-4-(1H-6-pyrimidinon-1-yl)-6-cyano-2H-chromene 2,2,3-trimethyl-4-(1H-6-pyrimidinon-1-yl)-6-cyano-chroman-3-ol 2,2,3-trimethyl-4-(1H-4-hydroxy-6-pyrimidinon-1-yl)-6-cyano-2H-chromene 2,2,3-trimethyl-4-(1H-4-hydroxy-6-pyrimidinon-1-yl)-6-cyano-chroman-3-ol 2,2,3-trimethyl-4-(1H-2-pyrazinon-1-yl)-6-cyano-2H-chromene 2,2,3-trimethyl-4-(1H-2-pyrazinon-1-yl)-6-cyano-chroman-3-ol 2,2,3 -trimethyl-4-(2-pyrrolidon-1-yl)-6-cyano-2H-chromene, m.p. 186°

2,2,3-trimethyl-4-(2-pyrrolidon-1-yl)-6-cyano-chroman-3-ol, m.p. 195°–197°

2,2,3-trimethyl-4-(2-piperidinon-1-yl)-6-cyano-2H-chromene 2,2,3-trimethyl-4-(2-piperidinon-1-yl)-6-cyano-chroman-3-ol 2,2-dimethyl-3-ethyl-4-(1H-2-pyridon-1-yl)-6-cyano-2-H-chromene 2,2-dimethyl-3-ethyl-4-(1H-2-pyridon-1-yl)-6-cyano-chroman-3-ol.

Example 28

A mixture of 21.5 g of IIb, 11.2 g of 3,6-pyridazinediol, 12 ml of pyridine and 600 ml of ethanol is boiled for 72 hours. About 300 ml of solvent is distilled off, the mixture is cooled, unreacted 3,6-pyridazinediol is filtered off and the filtrate is evaporated. The 2,2,3-trimethyl-4-(6-hydroxy-3-pyridazinyl-oxy)-6-cyano-chroman-3-ol [=2,2,3-Trimethyl-4-(1,6-dihydro-6-oxo-3-pyridazinyloxy)-6-cyano-chroman-3-ol] obtained is recrystallized from isopropanol. m.p. 240°.

The following are obtained analogously from the corresponding 3,4-epoxychromans:

2,3-dimethyl-4-(6-hydroxy-3-pyridazinyl-oxy)-chroman-3-ol 2,3-dimethyl-4-(6-hydroxy-3-pyridazinyl-oxy)-6-cyano-chroman-3-ol 2,3-dimethyl-4-(6-hydroxy-3-pyridazinyl-oxy)-6-nitro-chroman-3-ol 2,3-dimethyl-2-ethyl-4-(6-hydroxy-3-pyridazinyl-oxy)-6-cyanochroman-3-ol 2,2-diethyl-3-methyl-4-(6-hydroxy-3-pyridazinyl-oxy)-6-cyanochroman-3-ol 2,2-trimethylene-3-methyl-4-(6-hydroxy-3-pyridazinyl-oxy)-6-cyanochroman-3-ol 2,2-hexamethylene-3-methyl-4-( 6-hydroxy-3-pyridazinyl-oxy)-6-cyano-chroman-3-ol 2,2,3-trimethyl-4-(6-hydroxy-3-pyridazinyl-oxy)-chroman-3-ol 2,2,3 -trimethyl-4-(6-hydroxy-3-pyridazinyl-oxy)-6-methyl-chroman 3-ol 2,2,3-trimethyl-4-(6-hydroxy-3-pyridazinyl-oxy)-6-methoxy-chroman-3-ol 2,2,3-trimethyl-4-(6-hydroxy-3-pyridazinyl-oxy)-6-thioacetylchroman-3-ol 2,2,3-trimethyl-4-(6-hydroxy-3-pyridazinyl-oxy)-6-methoxy-thiocarbonyl-chroman-3-ol 2,2,3-trimethyl-4-(6-hydroxy-3-pyridazinyl-oxy)-6-thio(no)acetoxychroman-3-ol 2,2,3 -trimethyl-4-(6 -hydroxy-3-pyridazinyl-oxy)-6-hydroxymethylchroman-3-ol 2,2,3-trimethyl-4-(6-hydroxy-3-pyridazinyl-oxy)-6-dimethylaminochroman-3-ol 2,2,3-trimethyl-4-(6-hydroxy-3-pyridazinyl-oxy)-6-bromo-chroman-3-ol 2,2,3-trimethyl-4-(6-hydroxy-3-pyridazinyl-oxy)-6-iodo-chroman-3-ol 2,2,3-trimethyl-4-(6-hydroxy-3-pyridazinyl-6oxy)-6-methylsulfinylchroman-3-ol 2,2,3-trimethyl-4-(6-hydroxy-3-pyridazinyl-oxy)-6-methylsulfonylchroman-3-ol 2,2-dimethyl-3-hexyl-4-(6-hydroxy-3-pyridazinyl-oxy)-6-cyanochroman-3-ol

Example 29

A mixture of 10 g of "D", 3 g of sodium hydroxide and 350 ml of dioxane is boiled for 20 min. The mixture is cooled, filtered, and the filtrate is evaporated and "A" is obtained, m.p. 212°.

Example 30

A mixture of 2 g of "D", 11.7 ml of formic acid and 3.3 ml of acetic anhydride is allowed to stand at 20° for 16 hours and subsequently heated at 40°–42° for 2 hours. After evaporating and customary working up, 2,2,3-trimethyl- 3-formyloxy-4-(1H-2-pyridon-1-yl)-6-cyano-chroman is obtained.

The following are obtained analogously from the corresponding 3-hydroxy-chromans:

2,2,3-trimethyl-3-formyloxy-4-(1H-2-pyridon-1-yl)-6-nitro-chroman 2,2,3-trimethyl-3-formyloxy-4-(1H-4-hydroxy-2-pyridon-1-yl)-6-cyano-chroman 2,2,3-trimethyl-3-formyloxy-4-(1H-3-hydroxy-6-pyridazinon-1-yl)-6-cyano-chroman.

Example 31

A mixture of 1 g of "D" and 5 ml of acetic anhydride is boiled for 1 hour. The mixture is cooled, worked up as usual and 2,2,3-trimethyl-3-acetoxy-4-(1H-2-pyridon-1-yl)-6-cyano-chroman is obtained.

Example 32

2.96 g of "D" are suspended in 100 ml of water and 3.2 g of bromine are added dropwise with stirring at 10°–20°. Tie substance dissolves and 2,2,3-trimethyl-4-( 1H-3,5-dibromo-2-pyridon-1-yl)-6-cyano-chroman-3-ol precipitates and is filtered off.

Example 33

2.78 g of "C" are dissolved in a mixture of 10 ml of concentrated nitric acid (68%; density 1.41) and 12 ml of concentrated sulfuric acid, stirred at 20° for 3 hours and poured onto ice, the precipitate is filtered and washed with water, and a mixture of 2,2,3-trimethyl-4-(1H-3- and -5-nitro-pyridon-1-yl)-6-cyano-2H-chromene is obtained, which can be separated chromatographically.

Example 34

A solution of 1 g of 2,2,3-trimethyl-4-(4H-3-nitro-2-pyridon-1-yl)-6-methoxycarbonyl-chroman-3-ol in 25 ml of methanol is hydrogenated to completion at 20° and 1 bar on 0.5 g of 5% Pd-C. The mixture is filtered, the filtrate is evaporated and 2,2,3-trimethyl-4-(1H-3-amino-2 -pyridon-1-yl)-6-methoxycarbonyl-chroman-3-ol is obtained.

Example 35

A solution of 1 g of 2,2,3-trimethyl-4-(1H-3-amino-2-pyridon-1-yl)-6-cyano-2H-chromene in 15 ml of HCOOH and 1 ml of pyridine is boiled for 19 hours and evaporated. After customary working up, 2,2,3-trimethyl-4-(1H-3-formamido-2-pyridon-1-yl)-6-cyano-2H-chromene is obtained.

Example 36

A mixture of 1 g of 2,2,3-trimethyl-4-(1H-5-amino-2-pyridon-1-yl)-6-cyano-2H-chroman, 10 ml of acetic anhydride and 10 ml of pyridine is allowed to stand at 20° for 16 hours. The mixture is evaporated, the residue is purified chromatographically and 2,2,3-trimethyl-4-(1H-5-acetamido-2-pyridon-1-yl)-6-cyano-2H-chromene is obtained.

Example 37

HCl is passed into a boiling solution of 1 g of "A" in 50 ml of methanol and 2 ml of water with stirring for 14 hours. The mixture is allowed to cool and to stand overnight. The precipitated 2,2,3-trimethyl-4-(1H-2-pyridon-1-yl)-2H-chromene-6-carboxylic acid is filtered off.

Example 38

A mixture of 2.78 g of "C", 31 g of $Na_3PO_4.12 H_2O$, 28 ml of pyridine, 28 ml of water, 67 ml of acetic acid and 25 g of Raney Ni (moistened with water) is stirred at 20° for 3 hours. After filtering, customary working up gives 2,2,3-trimethyl-4-(1H-2-pyridon-1-yl)-6-formyl-2H-chromene.

The following are obtained analogously
2,2,3-trimethyl-4-(1H-2-pyridon-1-yl)-6-formyl-chroman-3-ol
2,2,3-trimethyl-4-(1H-2-pyridon-1-yl)-7-formyl-2H-chromene
2,2,3-trimethyl-4-(1H-2-pyridon-1-yl)-7-formyl-chroman-3-ol
2,2,3 -trimethyl-4-(1H-4-hydroxy-2-pyridon-1-yl)-6-formyl-2H-chromene
2,2,3 -trimethyl-4-(1H-4-hydroxy-2-pyridon-1-yl)-6-formylchroman-3-ol
2,2,3-trimethyl-4-(1H-3-hydroxy-6-pyridazinon-1-yl)-6-formyl- 2H-chromene
2,2,3-trimethyl-4-(1H-3-hydroxy-6-pyridazinon-1-yl)-6-formyl-chroman-3-ol.

Example 39

2.78 g of "C" are dissolved in 40 ml of tert.-butanol and 5.6 g of powdered KOH are added with stirring. After boiling for 1 hour and customary working up, 2,2,3 -trimethyl-4-(1H-2-pyridon-1-yl)-6-carbamoyl-2H-chromene is obtained.

The following are obtained analogously
2,2,3-trimethyl-4-(1H-2-pyridon-1-yl )-6-carbamoyl-chroman-3-ol
2,2,3-trimethyl-4-(1H-2-pyridon-1-yl)-7-carbamoyl-2H-chromene
2,2,3-trimethyl-4-(1H-2-pyridon-1-yl)-7-carbamoyl-chroman-3-ol
2,2,3-trimethyl-4-(1H-4-hydroxy-2-pyridon-1-yl)-6-carbamoyl-2H-chromene
2,2,3-trimethyl-4-(1H-4-hydroxy-2-pyridon-1-yl)-6-carbamoyl-chroman-3-ol
2,2,3-trimethyl-4-(1H-3-hydroxy-6 -piridazinon-1-yl)-6-carbamoyl-2 1 H-chromene
2,2,3-trimethyl-4-(1H-3-hydroxy-6-pyridazinon-1-yl)-6-carbamoyl-chroman-3-ol.

Example 40

$H_2S$ is passed into a solution of 2.78 g of "C" in a mixture of 20 ml of pyridine and 10 ml of triethylamine at 20° for 5 hours, the mixture is evaporated and worked up as usual, and 2,2,3-trimethyl-4-(1H-2-pyridon-1-yl)-6-thiocarbamoyl-2H-chromene is obtained.

The following are obtained analogously
2,2,3-trimethyl-4-(1H-2-pyridon-1-yl)-6-thiocarbamoylchroman-3-ol
2,2,3-trimethyl-4-(1H-2-pyridon-1-yl)-7-thiocarbamoyl-2H-chromene
2,2,3-trimethyl-4-(1H-2-pyridon-1-yl)-7-thiocarbamoylchroman-3-ol
2,2,3-trimethyl-4-(1H-4-hydroxy-2-pyridon-1-yl)-6-thiocarbamoyl-2H-chromene
2,2,3-trimethyl-4-(1H-4-hydroxy-6-pyridon-1-yl)-6-thiocarbamoyl-chroman-3-ol
2,2,3-trimethyl-4-(1H-3-hydroxy-6-pyridazinon-1-yl)-6-thiocarbamoyl-2 H-chromene
2,2,3-trimethyl-4-(1H-3-hydroxy-6-pyridazinon-1-yl)-6-thiocarbamoyl-chroman-3-ol

Example 41

A mixture of 310 mg of "D", 808 mg of Lawesson reagent and 50 ml of toluene is boiled under $N_2$ for 1 hour. Customary working up gives 2,2,3-trimethyl-4-(1H-2-thiopyridon-1-yl)-6-cyano-chroman-3-ol.

2,2,3-Trimethyl-4-(1H-2-thiopyridon-1-yl)-6-cyano-2H-chromene is obtained analogously from "C".

Example 42

The following are obtained analogously to Example 27:
2,2,3-trimethyl-4-(1H-4-methoxy-2-pyridon-1-yl)-6-cyano-2H-chromene
2,2,3-trimethyl-4-(1H-4-methoxy-2-pyridon-1-yl)-6-cyanochroman-3-ol
2,2,3-trimethyl-4-(1H-4-ethoxy-2-pyridon-1-yl)-6-cyano-2H-chromene
2,2,3-trimethyl-4-(1H-4-ethoxy-2-pyridon-1-yl)-6-cyanochroman-3-ol
2,2,3-trimethyl-4-(1H-4-acetoxy-2-pyridon-1-yl)-6-cyano-2H-chromene
2,2,3-trimethyl-4-(1H-4-acetoxy-2-pyridon-1-yl)-6-cyanochroman-3-ol
2,2,3-trimethyl-4-(1H-2-pyridon-1-yl)-6-cyano-8-nitro-2H-chromene
2,2,3-trimethyl-4-(1H-2-pyridon-1-yl)-6-cyano-8-nitrochroman-3-ol
2,2,3-trimethyl-4-(1H-2-pyridon-1-yl)-6-hydroxymethyl-2H-chromene
2,2,3-trimethyl-4-(1H-2-pyridon-1-yl)-6-hydroxymethylchroman-3-ol
2,2-tetramethylene-3-methyl-4-(1H-2-pyridon-1-yl)-6-nitro-2H-chromene
2 -tetramethylene-3-methyl-4 -(1H-2-pyridon-1-yl)-6-nitro-chroman- 3-ol
2,2-pentamethylene-3-methyl-(1H-2-pyridon-1-yl)-6 -nitro-2H-chromene
2,2-pentamethylene-3-methyl-4-(1H-2-pyridon-1-yl)-6-nitro-chroman-3-ol
2,2,3-trimethyl-4-(1H-3-methoxy-6-pyridazinon-1-yl)-6cyano-2H-chromene
2,2,3-trimethyl-4-(1H-3-methoxy-6-pyridazinon-1-yl)-6-cyano-chroman-3 -ol
2,2,3-trimethyl-4-(1H-4-hydroxy-2-pyridon-1-yl)-6-acetyl-2H-chromene 2,2,3-trimethyl-4-(1H-4-hydroxy-2-pyridon-1-yl)-6-acetylchroman-3-ol
2,2,3-trimethyl-4-(1H-4-hydroxy-2-pyridon-1-yl)-6-methoxycarbonyl-2H-chromene
2,2,3-trimethyl-4-(1H-4-hydroxy-2-pyridon-1-yl)-6-methoxycarbonyl-chroman-3-ol
2,2,3-trimethyl-4-(1H-4-hydroxy-2-pyridon-1-yl)-6-ethoxycarbonyl-2H-chromene
2,2,3-trimethyl-4-(1H-4-hydroxy-2-pyridon-1-yl )-6-ethoxycarbonyl-chroman-3-ol
2,2,3-trimethyl-4-(1H-3-hydroxy-6-pyridazinon-1-yl)-6-acetyl-2H-chromene
2,2,3-trimethyl-4-(1H-3-hydroxy-6-pyridazinon-1-yl)-6-acetyl-chroman-3-ol
2,2,3-trimethyl-4-(1H-3-hydroxy-6-pyridazinon-1-yl)-6-methoxycarbonyl-2H-chromene
2,2,3-trimethyl-4-(1H-3-hydroxy-6-pyridazinon-1-yl)-6-methoxycarbonyl-chroman-3-ol
2,2,3-trimethyl-4-(1H-3-hydroxy-6-pyridazinon-1-yl)-6-ethoxycarbonyl-2H-chromene
2,2,3-trimethyl-4-(1H-3-hydroxy-6-pyridazinon-1-yl)-6-ethoxycarbonyl-chroman-3-ol
2,2,3-trimethyl-4-(1H-3-hydroxy-6-pyridazinon-1-yl)-6-nitro-2H-chromene
2,2,3-trimethyl-4-(1H-3-hydroxy-6-pyridazinon-1-yl)-6-nitro-chroman-3-ol

Example 43

A mixture of 6.5 g of IIb, 3.1 g of pyridone, 3 ml of pyridine and 100 ml of ethanol is refluxed for 72 hours. After cooling and working up as usual, the mixture is chromatographed over silica gel. There is eluted with dichloromethane/petroleum ether (85:15) 2,2,3-trimethyl-4-(2-pyridyl-oxy)-6-cyano-chroman-3-ol (m.p. 105°–107°) subsequently with dichloromethane/ethyl acetate (85:15) "D", m.p. 185°–186°; weight ratio about 1:1.

Example 44

A mixture of 21.5 g of IIb, 11.1 g of 2,4-dihydroxypyridine (=4-hydroxy-1H-2-pyridone), 12 ml of pyridine and 360 ml of ethanol is refluxed for 48 hours. After cooling and working up as usual, the mixture is chromatographed over silica gel. 2,2,3-Trimethyl-4-(4-hydroxy-1H-2-pyridon-1-yl)-6-cyano-chroman-3-ol (m.p. 225°–227°) is eluted with dichloromethane/ethyl acetate (85:15), followed by 2,2,3-trimethyl-4-(1,2-dihydro-2-oxo-4-pyridyl-oxy)-6-cyanochroman-3-ol [2,2,3-trimethyl-4-(2-hydroxy-4-pyridyl-oxy-)-6-cyano-chroman-3-ol, F. 198°–200°, m.p. 198°–200°], with ethyl acetate/methanol (90:10); weight ratio about 1:9.

Example 45

Analogously to Example 28 there are obtained from IIa or from the corresponding 2,2,3-trimethyl-3,4-epoxy-chromanes with 3-hydroxypyridine:
2,2,3-trimethyl-4-(3-pyridyl-oxy)-6-cyano-chroman-3-ol;
with 4-hydroxypyridine:
2,2,3 - trimethyl-4-(4-pyridyl-oxy)-6-cyano-chroman-3-ol;
with 3-hydroxypyridazine:
2,2,3-trimethyl-4-(3-pyridazinyl-oxy)-6-cyano-chroman-3-ol;
with 4-hydroxypyrimidine:
2,2,3-trimethyl-4-(3-pyrimidinyl-oxy)-6-cyano-chroman-3-ol;
with 2-hydroxypyrazine:
2,2,3-trimethyl-4-(2-pyrazinyl-oxy)-6-cyano-chroman-3-ol;
with 2,4-dihydroxypyridine:
2,2,3-trimethyl-4-(2-hydroxy-4-pyridyl-oxy)-6-nitro-chroman-3-ol
2,2,3-trimethyl-4-(2-hydroxy-4-pyridyl-oxy)-6-bromochroman-3-ol
2,2,3-trimethyl-4-(2-hydroxy-4-pyridyl-oxy)-6-methoxycarbonyl-chroman-3-ol;
with 2,3-dihydroxypyridine:
2,2,3-trimethyl-4-(2-hydroxy-3-pyridyl-oxy)-6-cyanochroman-3-ol;
with 2,5-dihydroxypyridine:
2,2,3 - trimethyl-4-(2-hydroxy-5-pyridyl-oxy)-6-cyanochroman-3-ol;
with 4,6-dihydroxypyrimidine:
2,2,3-trimethyl-4-(6-hydroxy-4-pyrimidinyl-oxy)-6-cyano-chroman-3-ol;
with 3,6-dihydroxypyridine:
2,2,3-trimethyl-4-(6-hydroxy-3-pyridazinyl-oxy)-6-nitro-chroman-3-ol, m.p. 223°–225°
2,2-tetramethylene-3-methyl-4-(6-hydroxy-3-pyridazinyl-oxy)-6-cyano-chroman-3-ol
2,2-pentamethylene-3-methyl-4-(6-hydroxy-3-pyridazinyl-oxy)-6-cyano-chroman-3-ol, no m.p. until 275°
2,2,3-trimethyl-4-(6-hydroxy-3-pyridazinyl-oxy)-6-bromo-chroman-3-ol
2,2,3-trimethyl-4-(6-hydroxy-3-pyridazinyl-oxy)-6-methoxycarbonyl-chroman-3-ol.

Example 46

Analogously to Example 30, there are obtained by formylation of the corresponding chroman-3-ols:
2,2,3-trimethyl-3-formyloxy-4-(6-hydroxy-3-pyridazinyl-oxy)-6-cyano-chromane
2,2,3-trimethyl-3-formyloxy-4-(2-hydroxy-4-pyridyl-oxy)-6-cyano-chromane.

Example 47

Analogously to Example 31, these are obtained by acetylation of the corresponding chroman-3-ols:
2,2,3-trimethyl-6-acetoxy-4-(6-hydroxy-3-pyridazinyl-oxy)-6-cyano-chromane
2,2,3-trimethyl-6-acetoxy-4-(2-hydroxy-4-pyridyl-oxy)-6-cyano-chromane.

Example 48

A mixture of 327 mg of 2,2,3-trimethyl-4-(1,6-dihydro-6-oxo-3-pyridazinyl-oxy)-6-cyano-chroman-3-ol, 20 ml of acetone, 400 mg of $K_2CO_3$ and 0.2 ml of dimethyl sulfate is refluxed for 2 hours. The mixture is filtered, concentrated and chromatographed on silica gel. There is obtained with ethyl-acetate/methanol (9:1) 2,2,3-trimethyl-4-(1,6-dihydro-1-methyl-6-oxo-3-pyridazinyl-oxy)-6-cyanochroman-3-ol, m.p. 197°–199°.
Analogously, there are obtained by alkylation:
2,2,3-trimethyl-4-(1,2-dihydro-1-methyl-2-oxo-4-pyridyl-oxy)-6-cyano-chroman-3-ol
2,2,3-trimethyl-4-(1,2-dihydro-1-ethyl-2-oxo-4-pyridyl-oxy)-6-cyano-chroman-3-ol
2,2,3-trimethyl-4-(1,6-dihydro-1-ethyl-6-oxo-3-pyridazinyl-oxy)-6-cyano-chroman-3-ol, m.p. 166°–168°.

Example 49

A mixture of 20.1 g of "IIa", 14 g of pyridone, 7 ml of pyridine, and 70 ml of ethanol is boiled for 2 hours. The mixture is cooled, the precipitate of "B" is filtered off, the filtrate is concentrated, and the residue is chromatographed on silica gel. Using diethyl ether/ethyl acetate (1:1), 2,2-dimethyl-4-(2-pyridyloxy)-6-cyano-3-chromanol is obtained, m.p. 102°–103°.

The following are obtained analogously (boiling times up to 15 hours ):

2,2,3-Trimethyl-4- ( 2-pyridyloxy)-6-cyano-3-chromanol, m. p. 105°–107°

2,2-Tetramethylene-4-(2-pyridyloxy)-6-cyano-3-chromanol m.p. 126°–127°

2,2-Pentamethylene-4-(2-pyridyloxy)-6-cyano-3-chromanol, m.p. 108°–110°

2,2-Dimethyl-4-(2-pyridyloxy)-6-nitro-3-chromanol 2,2-Dimethyl-4-(2-pyridyloxy)-6-bromo-3-chromanol 2,2-Dimethyl-4-(2-pyridyloxy)-6-methoxycarbonyl-3-chromanol 2,2-Dimethyl-4-(3-pyridyloxy)-6-cyano-3-chromanol, m.p. 202°–204°

2,2,3-Trimethyl-4-(3-pyridyloxy)-6-cyano-3-chromanol 2,2-Dimethyl-4-(4-pyridyloxy)-6-cyano-3-chromanol, m.p. 193°–196°

2,2,3-Trimethyl-4-(4-pyridyloxy)-6-cyano-3-chromanol 2,2-Dimethyl-4-(3-pyridazinyloxy)-6-cyano-3-chromanol 3-Trimethyl-4-(3-pyridazinyloxy)-6-cyano-3-chromanol 2,2-Dimethyl-4-(4-pyrimidinyloxy)-6-cyano-3-chromanol, m.p. 193°–105°

2,2,3-Trimethyl-4-(4-pyrimidinyloxy)-6-cyano-3-chromanol 2,2-Dimethyl-4-(2-pyrazinyloxy)-6-cyano-3-chromanol, m.p. 103°–105°

2,2,3-Trimethyl-4-(2-pyrazinyloxy)-6-cyano-3-chromanol.

Example 50

A mixture of 20.1 g of IIa, 11.1 g of 2,4-dihydroxypyridine, 8 ml of pyridine and 400 ml of ethanol is boiled for 15 hours. The mixture is evaporated, the residue is extracted with ethyl acetate, the organic phase is washed with dilute hydrochloric acid and then with water, dried and evaporated, and 2,2-dimethyl-4-(2-hydroxy-4-pyridyloxy)-6-cyano-3-chromanol ("E") is obtained, m.p. 249°–249.5° (from ethanol).

The following are obtained analogously using 2,4-dihydroxypyridine:

2,2,3-Trimethyl-4-(2-hydroxy-4-pyridyloxy)-6-cyano-3 -chromanol, m.p. 198°–200°

2,2-Tetramethylene-4-(2-hydroxy-4-pyridyloxy)-6-cyano-3-chromanol 2,2 -Pentamethylene-4-(2-hydroxy-4-pyridyloxy)-6-cyano-3-chromanol 2,2-Dimethyl-4-(2-hydroxy-4-pyridyloxy)-6-nitro-3-chromanol, m.p. 224°–226°

2,2,3-Trimethyl-4-(2-hydroxy-4-pyridyloxy) -6-nitro-3-chromanol 2,2-Dimethyl-4-(2-hydroxy-4-pyridyloxy)-6-bromo-3-chromanol 2,2,3-Trimethyl-4-(2-hydroxy-4-pyridyloxy)-6-bromo-3-chromanol 2,2-Dimethyl-4-(2-hydroxy-4-pyridyloxy)-6-methoxycarbonyl-3-chromanol, m.p. 251°–252°

2,2,3-Trimethyl-4-(2-hydroxy-4-pyridyloxy)-6-methoxycarbonyl-3-chromanol;

using 2,3-dihydroxypyridine:

2,2-Dimethyl-4-(2-hydroxy-3-pyridyloxy)-6-cyano-3-chromanol, m.p. 262°–265°;

2,2,3-Trimethyl-4-(2-hydroxy-3-pyridyloxy)-6-cyano-3-chromanol;

using 2,5-dihydroxypyridine:

2,2-Dimethyl-4-(2-hydroxy-5-pyridyloxy)-6-cyano-3 -chromanol, m.p. 256°–258°;

2,2,3 -Trimethyl-4-(2-hydroxy-5-pyridyloxy)-6-cyano-3-chromanol;

using 4,6 dihydroxypyrimidine 2,2-Dimethyl-4-(6-hydroxy-4-pyrimidinyloxy)-6-cyano-3-chromanol, m.p. 235°–237°

2,2,3-Trimethyl-4-(6-hydroxy-4-pyrimidinyloxy)-6-cyano-3-chromanol;

using 3,6-dihydroxypyridazine:

2,2-Dimethyl-4-( 6-hydroxy-3-pyridazinyloxy )-6-cyano-3 -chromanol ("F"), m.p. 255°–256°

2,2,3-Trimethyl-4-(6-hydroxy-3-pyridazinyloxy)-6-cyano-3-chromanol, m.p. 236°–239°

2,2-Tetramethylene-4-(6-hydroxy-3-pyridazinyloxy)-6cyano-3-chromanol 2,2 - Pentamethylene-4-(6-hydroxy-3-pyridazinyloxy)-6-cyano-3-chromanol, no m.p. up to 275°

2,2 -Dimethyl-4-(6-hydroxy-3-pyridazinyloxy)-6-nitro-3-chromanol, no m.p. up to 260°

2,2,3-Trimethyl-4- ( 6-hydroxy-3-pyridazinyloxy) -6-nitro-3-chromanol, m.p. 223°–225°

2,2-Dimethyl-4-(6-hydroxy-3-pyridazinyloxy)-6-bromo-3-chromanol, m.p. 257°–259°

2,2,3-Trimethyl-4-(6-hydroxy-3-pyridazinyloxy) -6-bromo-3-chromanol 2,2-Dimethyl-4-(6-hydroxy-3-pyridazinyloxy)-6-methoxycarbonyl-3-chromanol, m.p. 242°

2,2,3-Trimethyl-4-(6-hydroxy-3-pyridazinyloxy)-6-methoxycarbonyl-3-chromanol.

Example 51

A mixture of 20.1 g of IIa, 11.1 g of 2-mercaptopyridine, 6.6 ml of pyridine and 265 ml of ethanol is boiled for 3 hours. The mixture is concentrated and the 2,2-dimethyl-4-(2-pyridylthio)-6-cyano-3-chromanol obtained is crystallized from diisopropyl ether, m.p. 101°–103°.

The following are obtained analogously:

2,2,3-Trimethyl-4-(2-pyridylthio)-6-cyano-3-chromanol 2,2-Dimethyl-4-(3-pyridylthio)-6-cyano-3-chromanol 2,2,3-Trimethyl-4-(3-pyridylthio)-6-cyano-3-chromanol 2,2-Dimethyl-4-(4-pyridylthio)-6-cyano-3-chromanol 2,2,3-Trimethyl-4-(4-pyridyl thio)-6-cyano-3-chromanol 2,2-Dimethyl-4-(2-hydroxy-4-pyridylthio)-6-cyano-3-chromanol 2,2,3 -Trimethyl-4-(2-hydroxy-4-pyridylthio)-6-cyano-3-chromanol 2,2 -Dimethyl-4-(6-hydroxy-3-pyridazinylthio)-6-cyano-3-chromanol 2,2,3-Trimethyl-4-(6-hydroxy-3-pyridazinylthio)-6-cyano-3-chromanol 2,2-Dimethyl-4-(6-mercapto-3-pyridazinylthio)-6-cyano-3-chromanol 2,2,3-Trimethyl-4-(6-mercapto-3-pyridazinylthio)-6-cyano-3-chromanol.

Example 52

A mixture of 2 g of IIa, 1.11 g of 2-mercaptopyridine, 60 ml of DMSO and 0.3 g of NaiI (80% strength) is stirred for 6 hours at 20° and worked up as customary. 2,2-Dimethyl-4-(2-pyridylthio)-6-cyano-3-chromene, m.p. 110°–112° is obtained.

The following are obtained analogously:

2,2,3-Trimethyl-4-(3-pyridylthio)-6-cyano-3-chromene
2,2-Dimethyl-4-(3-pyridylthio)-6-cyano-3-chromene
2,2,3-Trimethyl-4-(3-pyridylthio)-6-cyano-3-chromene
2,2-Dimethyl-4-(4-pyridylthio)-6-cyano-3-chromene
2,2,3-Trimethyl-4-(4-pyridylthio) -6-cyano-3-chromene
2,2-Dimethyl-4-(2-hydroxy-4-pyridylthio)-6-cyano-3-chromene
2,2,3-Trimethyl-4-(2-hydroxy-4-pyridylthio) -6-cyano-3-chromene
2,2-Dimethyl-4-(6-hydroxy-3-pyridazinylthio)-6-cyano-3-chromene
2,3-Trimethyl-4-(6-hydroxy-3-pyridazinylthio)-6-cyano-3-chromene
2,2-Dimethyl-4-(6-mercapto-3-pyridazinylthio)-6-cyano-3-chromene
2,2,3-Trimethyl-4-(6-mercapto-3-pyridazinylthio)-6-cyano-3-chromene.

Example 53

2,2-Dimethyl-4-(3-hydroxy-2-pyridylamino)-6-cyano-3-chromanol, m.p. 207°–208.5°, is obtained from IIa and 2-amino-3-hydroxypyridine analogously to Example 49.

The following are obtained analogously:

2,2,3-Trimethyl-4-(3-hydroxy-2-pyridylamino)-6-cyano-3-chromanol
2,2-Dimethyl-4-(2-hydroxy-4-pyrimidinylamino)-6-cyano-3-chromanol, no m.p. up to 280°
2,2,3-Trimethyl-4-(2-hydroxy-4-pyrimidinylamino)-6-cyano-3-chromanol
2,2 -Dimethyl-4-(2-hydroxy-4-pyridylamino)-6-cyano-3-chromanol
2,2,3-Trimethyl-4-(2-hydroxy-4-pyridylamino)-6-nitro-3-chromanol
2,2 -Dimethyl-4-(2-hydroxy-4-pyridylamino)-6-bromo-3-chromanol
2,2,3-Trimethyl-4 - ( 2 -hydroxy-4-pyridylamino ) -6-bromo-3-chromanol
2,2-Dimethyl-4-(6-hydroxy-3-pyridazinylamino)-6-cyano-3-chromanol
2,2,3 -Trimethyl-4-(6-hydroxy-3-pyridazinylamino)-6-cyano-3-chromanol
2,2-Dimethyl-4-(6-hydroxy-3-pyridazinylamino)-6-nitro-3-chromanol
2,2,3-Trimethyl-4-(6-hydroxy-3-pyridazinylamino)-6-nitro-3-chromanol
2,2-Dimethyl-4-(6-hydroxy-3-pyridazinylamino)-6-bromo-3-chromanol
2,2,3-Trimethyl-4-(6-hydroxy-3-pyridazinylamino)-6-bromo-3-chromanol The following are obtained analogously from 1,6-dihydro-3-imino-1-methyl-6-pyridazinone:

2,2-Dimethyl-4-(1,6-dihydro-6-oxo-3-pyridazinylamino)-6-cyano-3-chromanol
2,2,3-Trimethyl-4-(1,6-dihydro-6-oxo-3-pyridazinylamino)-6-cyano-3-chromanol
2,2-Dimethyl-4-(1,6-dihydro-6-oxo-3-pyridazinylamino)-6-nitro-3-chromanol
2,2,3 -Trimethyl-4-(1,6-dihydro-6-oxo-3-pyridazinylamino)-6-nitro-3-chromanol
2,2-Dimethyl-4-(1,6-dihydro-6-oxo-3-pyridazinylamino)-6-bromo-3-chromanol
2,2,3-Trimethyl-4-(1,6-dihydro-6-oxo-3-pyridazinylamino)-6-bromo-3-chromanol Example 54

1.2 g of 80% NaH are added to a solution of 2.66 g of 2,2-dimethyl-4-bromo-6-cyanochroman (m.p. 89°–92°; obtainable by reduction of 2,2-dimethyl-6-cyano-4-chromanone with NaBH$_4$, in CH$_3$OH to give oily 2,2-dimethyl-6-cyano-4-chromanol and reaction with PBr$_3$ in toluene at 20°) and 2.5 g of pyridazine-3,6-diol in 70 ml of DMSO and the mixture is stirred at 20° for 3 days. After customary working up, 2,2-dimethyl-4-(6-hydroxy-3-pyridazinyloxy)- 6-cyanochroman, m.p. 221°–224°, is obtained.

The following are obtained analogously:

with pyridazine-3,6-diol:

2,2,3-Trimethyl-4-(6-hydroxy-3-pyridazinyloxy)-6-cyanochroman
2,2-Dimethyl-4-(6-hydroxy-3-pyridazinyloxy)-6-bromochroman
2,2,3-Trimethyl-4-(6-hydroxy-3-pyridazinyloxy)-6-bromochroman
2,2-Dimethyl-4-(6-hydroxy-3-pyridazinyloxy)-6-nitrochroman
2,2,3-Trimethyl-4-(6-hydroxy-3-pyridazinyloxy)-6-nitrochroman;

with 2,4-dihydroxypyridine:

2,2-Dimethyl-4-(2-hydroxy-4-pyridyloxy)-6-cyanochroman
2,2,3-Trimethyl-4-(2-hydroxy-4-pyridyloxy)-6-cyanochroman
2,2-Dimethyl-4-(2-hydroxy-4-pyridyloxy)-6-bromochroman
2,2,3 -Trimethyl-4 -(2-hydroxy-4-pyridyloxy)-6-bromochroman
2,2-Dimethyl-4-(2-hydroxy-4-pyridyloxy)-6-nitrochroman
2,2,3-Trimethyl-4-(2 -hydroxy-4-pyridyloxy) -6-nitrochroman;

with pyridone:

2,2-dimethyl-4-(1H-2-pyridon-1-yl)-6-cyanochroman, m.p. 159°.

Example 55

A mixture of 10 g of 2,2-dimethyl-4-(2-pyridylthio)-6-cyano-3-chromanol, 3 g of sodium hydroxide a 350 ml of dioxane is boiled for 20-minutes. The mixture is cooled and filtered, the filtrate is evaporated and 2,2-dimethyl-4-(2-pyridylthio)-6-cyano-3-chromene, m.p. 110°–112°, is obtained.

Example 56

A mixture of 2 g of "F", 11.7 ml of formic acid and 3.3 ml of acetic anhydride is allowed to stand at 20° for 16 hours and then warmed to 40°–42° for 2 hours. After evaporating and customary working up, 2,2-dimethyl-3-formyloxy- 4-(6 -hydroxy-3-pyridazinyloxy)-6-cyanochroman is obtained.

The following are obtained analogously from the corresponding 3-hydroxychromans:

2,2,3-Trimethyl-3-formyloxy-4-(6-hydroxy-3-pyridazinyloxy)-6-cyanochroman
2,2 -Dimethyl-3-formyloxy-4-(2-hydroxy-4-pyridyloxy)-6-cyanochroman
2,2,3-Trimethyl-3-formyloxy-4-(2-hydroxy-4-pyridyloxy)-6-cyanochroman.

Example 57

A mixture of 1 g of "F" and 5 ml of acetic anhydride is boiled for 1 hour. The mixture is cooled, worked up as customary and 2,2-dimethyl-3-acetoxy-4-(6-hydroxy-3-pyridazinyloxy)-6-cyanochroman is obtained The following are obtained analogously:
2,2,3-Trimethyl-3-acetoxy-4-(6-hydroxy-3-pyridazinyloxy)-6-cyanochroman
2,2-Dimethyl-3-acetoxy-4-(2-hydroxy-4-pyridyloxy)-6-cyanochroman
2,2,3-Trimethyl-3-acetoxy-4-(2-hydroxy-4-pyridyloxy)-6-cyanochroman.

Example 58

A solution of 1 g of 2,2-dimethyl-4-(2-hydroxy-4-pyridyloxy )-6-nitro-3-chromanol in 25 ml of methanol is hydrogenated at 20° and 1 bar on 0.5 g of 5% Pd-C to completion. The mixture is filtered, evaporated and 2,2-dimethyl-4-(2-hydroxy-4-pyridyloxy)-6-amino-3-chromanol is obtained.

The following are obtained analogously:
2,2,3-Trimethyl-4-(2-hydroxy-4-pyridyloxy)-6-amino-3-chromanol
2,2-Dimethyl-4-(6-hydroxy-3-pyridazinyloxy)-6-amino-3-chromanol
2,2,3-Trimethyl-4-(6-hydroxy-3-pyridazinyloxy)-6-amino-3-chromanol.

Example 59

A solution of 1 g of 2,2-dimethyl-4-(2-hydroxy-4-pyridyloxy)-6-amino-3-chromanol in 15 ml of HCOOH and 1 ml of pyridine is boiled for 19 hours and evaporated. After customary working up, 2,2-dimethyl-4 - ( 2-hydroxy-4-pyridyloxy)-6-formamido-3-chromanol is obtained.

Example 60

A mixture of 1 g of 2,2-dimethyl-4-(2-hydroxy-4-pyridyloxy)-6-amino-3-chromanol, 10 ml of acetic anhydride and 10 ml of pyridine is allowed to stand at 20° for 16 hours. The mixture is evaporated, purified chromatographically and 2,2-dimethyl-4-(2-hydroxy-4-pyridyloxy)-6-acetamido-3-chromanol is obtained.

Example 61

HCl is introduced with stirring for 14 hours into a boiling solution of 1 g of "E" in 50 ml of methanol and 2 ml of water. The mixture is allowed to cool and stand overnight. The 2,2-dimethyl-4-(6-hydroxy-3-pyridazinyl-oxy)-3-chromanol-6-carboxylic acid deposited is filtered off.

Example 62

A mixture of 3.13 g of "F", 31 g of $Na_3PO_4.12\ H_2O$, 28 ml of pyridine, 28 ml of water, 67 ml of acetic acid and 25g of Raney Ni (water-moist) is stirred at 20° for 3 hours. After filtering, the mixture is worked up as customary and 2,2-dimethyl-4-(6-hydroxy-3-pyridazinyloxy)-6-formyl-3-chromanol, m.p. 256°–257°, is obtained.

The following are obtained analogously:
2,2,3-Trimethyl-4-(6-hydroxy-3-pyridazinyloxy)-6-formyl-3-chromanol
2,2-Dimethyl-4-(2-hydroxy-4-pyridyloxy)-6-formyl-3-chromanol
2,2,3-Trimethyl-4-(2-hydroxy-4-pyridyloxy)-6-formyl-3-chromanol

Example 63

3.13 g of "F" are dissolved in 40 ml of tert.butanol and 5.6 g of powdered KOH are added with stirring. After boiling for 1 hour and customary working up, 2,2-dimethyl-4-(6-hydroxy-3-pyridazinyloxy)-6-carbamoyl-3-chromanol is obtained.

The following are obtained analogously:
2,2,3-Trimethyl-4-(6-hydroxy-3-pyridazinyloxy)-6-carbamoyl-3-chromanol
2,2-Dimethyl-4-(2 -hydroxy-4-pyridyloxy)-6-carbamoyl-3-chromanol
2,2,3-Trimethyl-4-(2-hydroxy-4-pyridyloxy)-6-carbamoyl- 3-chromanol.

Example 64

$H_2S$ is introduced at 20° for 5 hours into a solution of 3.12 g of "E" in a mixture of 20 ml of pyridine and 10 ml of triethylamine, the mixture is evaporated and worked up as customary, and 2,2-dimethyl-4-(2-hydroxy-4-pyridyloxy)-6-thiocarbamoyl-3-chromanol, m.p. 242°, is obtained.

The following are obtained analogously:
2,2,3-Trimethyl-4-(2-hydroxy-4-pyridyloxy)-6-thiocarbamoylchroman-3-ol.
2,2-Dimethyl-4-(6-hydroxy-3-pyridazinyloxy)-6-thiocarbamoyl-3-chromanol, m.p. 142°–144°
2,2,3-Trimethyl-4-(6-hydroxy-3-pyridazinyloxy)-6-thiocarbamoyl-3-chromanol.

Example 65

A mixture of 310 mg of "F", 808 mg of Lawesson reagent and 50 ml of toluene is boiled under $N_2$ for 1 hour, customary working up gives 2,2-dimethyl-4-(6-mercapto-3-pyridazinyloxy)-6-cyano-3-chromanol [2,2-dimethyl-4-(1,6-dihydro-6-thioxo-3-pyridazinyloxy)-6-cyano-3-chromanol].

2,2-Dimethyl-4-(2-mercapto-4-pyridyloxy)-6-cyano-3-chromanol is obtained analogously from 'E".

The following are obtained analogously:
2,2,3-Trimethyl-4-(6-mercapto-3-pyridazinyloxy)-6-cyano-3-chromanol
2,2-Dimethyl-4-(6-mercapto-3-pyridazinyloxy)-6-nitro-3-chromanol
2,2,3-Trimethyl-4-(6-mercapto-3-pyridazinyloxy)-6-nitro-3-chromanol
2,2-Dimethyl-4-(6-mercapto-3-pyridazinyloxy)-6-bromo-3-chromanol
2,2,3-Trimethyl-4-(6-mercapto-3-pyridazinyloxy)-6-bromo-3-chromanol
2,2,3-Trimethyl-4-(2-mercapto-4-pyridyloxy)-6-cyano-3-chromanol
2,2 -Dimethyl-4-(2 -mercapto- 4-pyridyloxy)-6-nitro-3 -chromanol
2,2,3-Trimethyl-4-(2-mercapto-4-pyridyloxy)-6-nitro-3-chromanol
2,2-Dimethyl-4-(2-mercapto-4-pyridyloxy)-6-nitro-3-chromanol
2,2,3 -Trimethyl-4-(2 -mercapto-4-pyridyloxy)-6-nitro-3-chromanol.

Example 66

A mixture of 312 mg of "E", 20 ml of acetone, 400 mg of $K_2CO_3$ and 0.2 ml of dimethyl sulfate is boiled for 2 hours. The mixture is filtered, evaporated and chromatographed on silica gel. Using ethyl acetate/methanol (9:1), 2,2-dimethyl-4-(1,2-dihydro-1-methyl-2- oxo-4-pyridyloxy)-6-cyano-3-chromanol, m.p. 202°–203°, is obtained.

The following are obtained analogously:

2,2,3-Trimethyl-4-(1,2-dihydro-1-methyl-2-oxo-4-pyridyloxy)-6-cyano-3-chromanol 2,2-Dimethyl-4-(1,6-dihydro-1-methyl-6-oxo-3-pyridazinyloxy)-6-cyano-3-chromanol, m.p. 206°–208°

2,2,3-Trimethyl-4-(1,6-dihydro-1-methyl-6-oxo-3-pyridazinyloxy)-6-cyano-3-chromanol, m.p. 197°–199°

2,2-Dimethyl-4-(1,6-dihydro-1-methyl-6-oxo-3-pyridazinyloxy)-6-nitro-3-chromanol 2,2,3-Trimethyl-4-(1,6-dihydro-1-methyl-6-oxo-3-pyridazinyloxy)-6-nitro-3-chromanol 2,2-Dimethyl-4-(1,6-dihydro-1-methyl-6-oxo-3-pyridazinyloxy)-6-bromo-3-chromanol 2,2,3-Trimethyl-4-(1,6-dihydro-1-methyl-6-oxo-3-pyridazinyloxy)-6-bromo-3-chromanol 2,2-Dimethyl-4-(1,2-dihydro-1-ethyl-2-oxo-4-pyridyloxy)-6-cyano-3-chromanol 2,2,3-Trimethyl-4-(1,2-dihydro-1-ethyl-2-oxo-4-pyridyloxy)-6-cyano-3-chromanol 2,2-Dimethyl-4-(1,2-dihydro-1-ethyl-6-oxo-3-pyridazinyloxy)-6-cyano-3-chromanol, m.p. 164°–167°

2,2,3-Trimethyl-4-(1,2-dihydro-1-ethyl-6-oxo-3-pyridazinyloxy)-6-cyano-3-chromanol, m.p. 166°–168°

Example 67

A mixture of 313 mg of "F", 1 g of $K_2CO_3$, 0.65 ml of dimethyl sulfate and 16 ml of DMF is boiled for 3 hours and worked up as customary. 2,2-Dimethyl-4-(6-methoxy-3-pyridazinyloxy)-6-cyano-3-chromanol, m.p. 224°–227°, is obtained.

The following are obtained analogously:

2,2,3-Trimethyl-4-(6-methoxy-3-pyridazinyloxy)-6-cyano-3-chromanol 2,2-Dimethyl-4-(2-methoxy-4-pyridyloxy)-6-cyano-3-chromanol 2,2,3-Trimethyl-4-(2-methoxy-4-pyridyloxy)-6-cyano-3-chromanol.

Example 68

In analogy to Example 66, 2,2-dimethyl-4-(1,6-dihydro-1-isopropyl-6-oxo-3-pyridazinyloxy)-6-cyano-3-chromanol is obtained from "F" and 2-bromopropane; m.p. 201°–203°

Example 69 a) A mixture of 5 g of "F", 5 g of (+)-campher-10-sulfonic chloride and 50 ml of pyridine is warmed to 70° for 5 hours. After working up with dilute hydrochloric acid and ethyl acetate as usual and chromatographic separation on silica gel with mixtures of dichloromethane and ethyl acetate, there are obtained two epimers of "F"—(+)-campher-10-sulfonic acid ester, m.p. 223°–224° and m.p. 127°–150°, respectively.

b) A mixture of 2 g of the "unpolar" epimer (m.p. 223°–224°), 16 g of "sodium hydroxide on carrier" ("Natriumhydroxid auf Träger", E. Merck, catalogue "Reagenzien, Diagnostica, Chemikalien", 1987/88, page 587, No. 1567) and 80 ml of methanol is stirred for 20 hours at 20°. The mixture is concentrated to dryness and dissolved in water. HCl is added until pH 8 and the 2,2-dimethyl-4-(1,6-dihydro-6-oxo-3-pyridazinyloxy)-6-cyano-3-chromene thus obtained (m.p. 226°–228°) is filtered off. Working up of the filtrate with hydrochloric acid/ethyl acetate at pH 4 and chromatography on silica gel with dichloromethane/ethyl acetate/methanol yields (−)-2,2-dimethyl-4-(1,6-dihyro-6-oxo-pyridazinyl-oxy)-6-cyano-3-chromanol, m.p. 229°; $[\alpha] -168.5°$.

c) Analogously, (+)-2,2-dimethyl-4-(1,6-dihydro-6-oxo-3-pyridazinyl-oxy)-6-cyano-3-chromanol (m.p. 232°–233°; $[\alpha]+170.0°$) is obtained from the "polar" epimer (m.p. 127°–150°).

Analogously, 2,2-dimethyl-4-(2-hydroxy-4-pyridyl-oxy)-6-cyano-3-chromene (m.p. 263°–264°) as well as (−)- and (+)-2,2-dimethyl-4-(2-hydroxy-4-pyridyl-oxy)-6-cyano-3-chromanol are obtained from "E" via the corresponding (+)-campher-sulfonic acid esters.

Analogously, 2,2-dimethyl-4-(1,6-dihydro-1-methyl-5-oxo-3-pyridazinyl-oxy)-6-cyano-3-chromene (m.p. 144°–146°) as well as (−)-2,2-dimethyl-4R-(1,6-dihydro-1-methyl-6-oxo-3-pyridazinyl-oxy)-6-cyano-3S-chromanol (m.p. 161°–164°; $[\alpha -173.7°]$) and (+)-2,2-dimethyl-4S-(1,6-dihydro-1-methyl-6-oxo-3-pyridazinyl-oxy)-6-cyano-3R-chromanol (m.p. 161°–162°; $[\alpha]+171.8°$) are obtained from 2,2-dimethyl-4-(1,6-dihydro-1-methyl-6-oxo-3-pyridazinyl-oxy)-6-cyano-3-chromanol via the corresponding (+)-camphersulfonic acid esters.

Analogously, 2,2,3-trimethyl-4-(1,6-dihydro-6-oxo-3-pyridazinyl-oxy)-6-cyano-3-chromene as well as (−)-2,2,3-trimethyl-4-(1,6-dihydro-6-oxo-3-pyridazinyl-oxy)-6-cyano-3-chromanol (m.p. 131°–134°; $[\alpha] -222.2°$) and (+)-2,2,3-trimethyl-4-(1,6-dihydro-6-oxo-3-pyridazinyl-oxy)-6-cyano-3-chromanol (m.p,131°–134°; $[\alpha]+222.2°$) are obtained from the racemic chromanol.

Example 70

Methyl iodide (4ml) is added to a mixture of 1 g of "B", 0.7 g of K-tert.-butylate and 200 ml toluene. After stirring for 3 hours at boiling temperature, the mixture is cooled and worked up in the customary manner. 2,2-Dimethyl-3-methoxy-4-(1H-2-pyridon-1-yl)-6-cyano-chroman is obtained: m.p. 169°–171°.

The examples below relate to pharmaceutical formulations containing compounds of the formula I or their physiologically acceptable salts:

Example A Tablets

A mixture of 1 kg of 2,2-dimethyl-4-(1H-2-pyridon-1-yl)-6-cyano-2H-chromene ("A"), 4 kg of lactose, 1.2 kg of potato starch, 0.2 g of talc and 0.1 kg of magnesium stearate is compressed in the customary manner to give tablets in such a way that each tablet contains 0.1 mg of active compound.

Example B Coated tablets

Tablets are compressed analogously to Example A and are then coated in the customary manner with a coating composed of sucrose, potato starch, talc, tragacanth gum and colorant.

Example C Capsules 1 kg of 2,2-dimethyl-4-(1H-2-pyridon-1-yl)-6-cyano-chroman-3-ol ("B") is filled into hard gelatine capsules in the customary manner in such a way that each capsule contains 0.5 mg of active compound.

Example D Ampoules

A solution of I kg of 2,2-dimethyl-4-(1H-2-pyridon-1-yl)-6-nitro-2H-chromene in a mixture of 20 l of 1,2-propanediol and 10 l of twice-distilled water is filtered under sterile conditions and filled into ampoules, which are lyophilized and sealed under sterile conditions. Each ampoule contains 0.1 mg of active compound.

Tablets, coated tablets, capsules or ampoules containing one or more of the remaining active compounds of the formula I and/or their physiologically acceptable salts can also be obtained analogously.

Example E Solution for topical application (against alopecia)

500 g of "A" (or "B") are dissolved in a mixture of 5.2 kg of 1,2-propanediol and 15 l of ethanol, and the mixture is made up to 25 l with ethanol, filtered under sterile conditions and filled into bottles.

Example F Gel 0.45 g of Carbopol 934 P (=carboxyvinyl polymer) is mixed with 40 ml of twice-distilled water and 27 ml of ethanol, a solution of 0.5 g of "A" (or "B") and 0.45 g of diisopropanolamine in 10 ml of 1,2-propanediol and 13 ml o f ethanol is added and mixed thoroughly, and the mixture is made up to 100 ml with water and again mixed thoroughly. The resulting gel contains 0.5% by weight of active compound.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is
1. A chroman of the formula

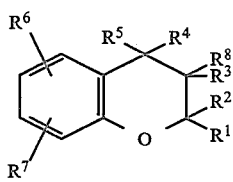

wherein
$R^1$ is A,
$R^2$ is H or A,
$R^1$ and $R^2$ together are also alkylene having 3–6 C atoms,
$R^3$ is OH or OAc,
$R^4$ is H, or
$R^3$ and $R^4$ together are a bond,
$R^5$ is pyrazinon-1-yl which is unsubstituted or monosubstituted or disubstituted by A, F;
$R^6$ and $R^7$ are each H, A, HO, AO, CHO, ACO, ACS, HOOC, AOOC, AO-CS, ACOO, A-CS-O, hydroxyalkyl having 1–6 C atoms, mercaptoalkyl having 1–6 C atoms, $NO_2$, $NH_2$, HA, $NA_2$, CN, F, Cl, Br, I, $CF_3$, ASO, $ASO_2$, AO-SO, AO-$SO_2$, AcNH, AO-CO-NH, $H_2NSO$, HANSO, ANSO, $H_2NSO_2$, $HANSO_2$, $A_2NSO$, $H_2NCO$, HANCO, $A_2NCO$, $H_2NCS$, HANCS, $A_2NCS$, ASONH, $ASO_2NH$, AOSONH, $AOSO_2NH$, ACO-alkyl, nitroalkyl, cyanoalkyl, A-C(=NOH) or A-C(=$NNH_2$),
$R^8$ is H
A is alkyl having 1–6 C atoms;
alkyl is of 1–6 C atoms; and
Ac is alkanoyl having 1–8 C atoms or aroyl having 7–11 C atoms, or a physiologically acceptable salt thereof.

2. A chroman according to claim 1, wherein $R^1$ and $R^2$ are each $CH_3$.

3. A chroman according to claim 2, wherein
$R^3$ is OH,
$R^4$ is H, or
$R^3$ and $R^4$ together are a bond,
$R^5$ is 1H-2-pyrazinon-1-yl,
$R^6$ is 6-CN,
$R^7$ is H and
$R^8$ is H.

4. A chroman according to claim 1, wherein $R^3$ is OH, OCHO or OCOCH$_3$ and $R^4$ is H.

5. A chroman according to claim 1, wherein $R^3$ and $R^4$ together are a bond.

6. 2,2-Dimethyl-4-(1H-2-pyrazinon-1-yl)-6-cyano-2H-chromene.

7. 2,2-Dimethyl-4-(1H-2-pyrazinon-1-yl)-6-cyano-3-chromanol.

8. A pharmaceutical composition comprising a compound of claim 1 and a pharmaceutically acceptable carrier.

9. A method of inducing a hypotensive effect comprising administering a compound of claim 1.

10. A chroman of the formula

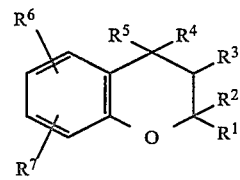

wherein
$R^1$ is A;
$R^2$ is H or A;
$R^1$ and $R^2$ alternatively are together alkylene having 3–6 C atoms;
$R^3$ is OH or OAc;
$R^4$ is H;
$R^3$ and $R^4$ alternatively are together a bond;
$R^5$ is pyrazinyloxy;
$R^6$ and $R^7$ are each independently H, A, HO, AO, CHO, ACO, ACS, HOOC, AOOC, AO-CS, ACOO, A-CS-O, hydroxyalkyl having 1–6 C atoms, mercaptoalkyl having 1–6 C atoms, $NO_2$, $NH_2$, NHA, $NA_2$, CN, F, Cl, Br, I, $CF_3$, ASO, $ASO_2$, AO-SO, AO-$SO_2$, AcNH, AO-CO-NH, $H_2NSO$, HANSO, $A_2NSO$, $H_2NSO_2$, $HANSO_2$, $A_2NSO_2$, $H_2NCO$, HANCO, $A_2NCO$, $H_2NCS$, HANCS, $A_2NCS$, ASONH, $ASO_2NH$, AO-SONH, $AOSO_2NH$, ACO-alkyl, nitroalkyl, cyanoalkyl, A-C(=NOH) or A-C(=$NNH_2$);

A is alkyl having 1–6 C atoms;
alkyl is alkylene having 1–6 C atoms; and
Ac is alkanoyl having 1–8 C atoms or aroyl having 7–11 C atoms,
or a physiologically acceptable salt thereof.

11. A chroman according to claim 10, wherein $R^1$ and $R^2$ are each $CH_3$.

12. A chroman according to claim 10, wherein $R_3$ is OH, OCHO or OCOCH$_3$ and $R^4$ is H.

13. A chroman according to claim 11, wherein
$R^3$ is OH,
$R^4$ is H, or
$R^3$ and $R^4$ together are a bond,
$R^5$ is 1H-2-pyrazinon-1-yl,
$R^6$ is 6-CN,
$R^7$ is H and
$R^8$ is H.

14. A chroman according to claim 10, wherein $R^3$ and $R^4$ together are a bond.

15. A pharmaceutical composition comprising a compound of claim 10 and a pharmaceutically acceptable carrier.

16. A method of inducing a hypotensive effect comprising administering a compound of claim 10.

17. A chroman of the formula

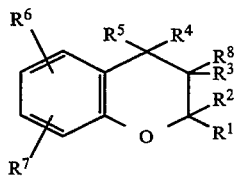

wherein
$R^1$ is A,
$R^2$ is H or A,
$R^1$ and $R^2$ together are also alkylene having 3–6 C atoms,
$R^3$ is OH or OAc;
$R^4$ is H, or
$R^3$ and $R^4$ together are a bond,
$R^5$ is a 1-H2-pyrazian-1-yl;
$R^6$ and $R^7$ are each H, A, HO, AO, CHO, ACO, ACS, HOOC, AOOC, AO-CS, ACOO, A-CS-O, hydroxyalkyl having 1–6 C atoms, mercaptoalkyl having 1–6 C atoms, $NO_2$, $NH_2$, NHA, $NA_2$, CN, F, Cl, Br, I, $CF_3$, ASO, $ASO_2$, AO-SO, $AO-SO_2$, AcNH, AO-CO-NH, $H_2NSO$, HANSO, $A_2NSO$, $H_2NSO_2$, $HANSO_2$, $A_2NSO_2$, $H_2NCO$, HANCO, $A_2NCO$, $H_2NCS$, HANCS, $A_2NCS$, ASONH, $ASO_2NH$, AOSONH, $AOSO_2NH$, ACO-alkyl, nitroalkyl, cyanoalkyl, A-C(=NOH) or A-C(=$NNH_2$),
$R^8$ is A
A is alkyl having 1–6 C atoms;
alkyl is of 1–6 C atoms; and
Ac is alkanoyl having 1–8 atoms or aroyl having 7–11 atoms, or a physiologically acceptable salt thereof.

18. A chroman of the formula

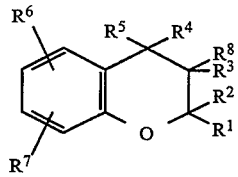

wherein
$R^1$ is A,
$R^2$ is H or A,
$R^1$ and $R^2$ together are also alkylene having 3–6 C atoms,
$R^3$ is H, OH, OA or OAc,
$R^4$ is ,
$R^3$ and $R^4$ together are also a bond,
$R^5$ is pyrazinyl-Z-;
$R^6$ and $R^7$ are each H, A, HO, AO, CHO, ACO, ACS, HOOC, AOOC, AO-CS, ACOO, A-CS-O, hydroxyalkyl having 1–6 C atoms, mercaptoalkyl having 1–6 1 C atoms, $NO_2$, $NH_2$, NHA, $NA_2$, CN, F, cl, Br, I, $CF_3$, ASO, $ASO_2$, AO-SO, $AO-SO_2$, AcNH, AO-CO-NH, $H_2NSO$, HANSO, $A_2NSO$, $H_2NSO_2$, $HANSO_2$, $A_2NSO_2$, $H_2NCO$, HANCO, $A_2NCO$, $H_2NCS$, HANCS, $A_2NCS$, ASONH, $ASO_2NH$, AOSONH, $AOSO_2NH$, ACO-alkyl, nitroalkyl, cyanoalkyl, A-C(=NOH) or A-C(=$NNH_2$),
Z is O;
A is alkyl having 1–6 C atoms;
alkyl is of 1–6 C atoms; and
Ac is alkanoyl having 1–8 atoms or aroyl having 7–11 atoms, or a physiologically acceptable salt thereof.

* * * * *

UNITED STATES PATENT AND TRADEMARK OFFICE
CERTIFICATE OF CORRECTION

PATENT NO. : 5,387,587
DATED : 02/07/95
INVENTOR(S) : Gunter HAUSLER et al.

It is certified that error appears in the above-indentified patent and that said Letters Patent is hereby corrected as shown below:

Claim 1; column 43, line 54: After "is" insert -- 1H-2- --.

Claim 1; column 43, line 54: After "1H-2-pyrazinon--1-yl" delete remainder of lines -- 54-55 --.

Claim 1; column 43, line 59: Change "HA" to -- NHA --.

Claim 1; column 43, line 61: Change "ANSO" to -- $A_2NSO$ --.

Claim 17; column 45, line 34: Change "pyrazian" to -- pyrazinon --.

UNITED STATES PATENT AND TRADEMARK OFFICE
CERTIFICATE OF CORRECTION

PATENT NO. : 5,387,587
DATED : 02/07/95
INVENTOR(S) : Gunter HAUSLER et al.

It is certified that error appears in the above-indentified patent and that said Letters Patent is hereby corrected as shown below:

Claim 17; column 45, line 41: Change "$H_2NSO_{21}$, HANSO2," to - -$H_2NSO_2$, $HANSO_2$ - -.

Claim 18; column 46, line 24: After "is" insert - - H - -.

Signed and Sealed this

Twelfth Day of September, 2000

Attest:

Q. TODD DICKINSON

*Attesting Officer*     *Director of Patents and Trademarks*